US005773002A

United States Patent [19]
Thomas et al.

[11] Patent Number: 5,773,002
[45] Date of Patent: Jun. 30, 1998

[54] CLONING AND SEQUENCING OF ALLERGENS OF DERMATOPHAGOIDES (HOUSE DUST MITE)

[75] Inventors: Wayne R. Thomas, Nedlands; Kaw-Yan Chua, Nollamara, both of Australia

[73] Assignees: The Institute of Child Health Research, West Perth, Australia; Immulogic Pharmaceutical Corporation, Waltham, Mass.

[21] Appl. No.: 461,441

[22] Filed: Jun. 5, 1995

Related U.S. Application Data

[60] Division of Ser. No. 945,288, Sep. 10, 1992, Pat. No. 5,433,948, which is a continuation-in-part of Ser. No. 580, 655, Sep. 11, 1990, abandoned, which is a continuation-in-part of Ser. No. 458,642, Feb. 13, 1990, abandoned.

[30] Foreign Application Priority Data

Sep. 10, 1991 [WO] WIPO ..................... PCT/AU91/00417

[51] Int. Cl.⁶ .................................................. A61K 39/35
[52] U.S. Cl. .................................... 424/184.1; 424/185.1; 424/200.1; 424/275.1; 530/350; 530/324; 530/325; 530/326; 530/327; 530/328; 435/69.1; 435/172.3
[58] Field of Search ............................. 424/185.1, 192.1, 424/184.1, 200.1, 275.1; 530/350, 858, 324–328; 436/547, 513, 826; 435/68.1, 69.1, 69.3, 69.7, 69.8, 71.1, 172.3, 252.3

[56] References Cited

U.S. PATENT DOCUMENTS 5,026,545  6/1991  Saint-Remy et al. ................... 424/85.8

FOREIGN PATENT DOCUMENTS

A 50598/90  2/1990  Australia .
A 71277/91  2/1991  Australia .

OTHER PUBLICATIONS

Chapman, et al. "II. Mite Alergens", The UCB Institute of Allergy, Bad Kreznach, Sep. 1–2, 1987.
Chua, et al., (1988) Chemical Abstracts, 105: 148, (Abstract).
Chua, et al, (1990) "Expression of *Dermatophagoides pteronyssinus* Allergen, Der p. II. in *Escherichia coli* and the Binding Studies with Human IgE" *Int. Arch. Allergy Appl. Immunol.* 91(2):124–9 (Abstract).
Chua, et al, (1991) "IgE binding studies with large peptides expressed from der p II cDNA constructs", *Clinical and Experimental Allergy* 21:161–166.
Chua, et al. (1990) "Isolation of cDNA Coding for the Major Mite Allergen Der p II by IgE Plaque Immunoassay", *Internationall Arch. of Allergy & Applied Immunol.*, 91:118–123.
Ford, et al. (1989) "The Spectrum of Low Molecular Weight House Dust Mite Allergens with Emphasis on Der p II" *Clin. and Exerimental Allergy*, 20:27–31.

Greene, et al. (1992) "IgE Binding Structures of the Major House Dust Mite Allergen Der p I" *Molecular Immunology* 29(2):257–262.
Greene, et al. "IgE and EgG binding of peptides expressed from fragments fo cDNA encoding the major house dust mite allergen der p I" *The J. of Immunology* 147: 3768–3773.
Gurka, et al, (1989) "Allergen–specific Human T Cell Clones: Derivation, Specificity, and Activation Requirements" *J Allergy Clin Immunol* 83(5):945–954.
Heymann, et al. Antigen Der f I from theust mite Dermatophagoides Farinae: structural comparison with Der p I from Dermatophagoides Pteronyssinus and Epitope Specificity . . . antibodies: *J. of Immunol.* 9:2841–47.
Krillis et al, (1984) "Antigens and Allergens from the Common House Dust Mite *Dermatophagoides pteronyssinus*" *J. of Aller. Clin, Immunol.* Aug. p. 142–146.
Lamb, et al. (1988) "The use of nitrocellulose immunoblots for the analysis of antigen recognition by T Lymphocytes" *J. of Immun. Methods* 110(1):1–10.
Lamb, et al. (1989) "HLA class II restriction specificity of Dermatophagoides spp. reactive T lymphocyte clones that support IgE synthesis" *Clin. and Experim. Allergy*, 19:389–393.
O'Hehir, et al. (1989) "Clonal Analysis of the Cellular Immune Response to the House Dust Mite *Dermatophagoides farinae*" *Int. Arch. Allergy Appl. Immunol.*, 88:170–172.
Pierce, et al. (1986) "Molecular cloning fo Schistosoma" *Biochem. Genetics*, 108: 191 (Abstract).
Rosenwasser, Lanny J., (1991) "Molecular Biology of Allergen Characterization" Post Graduate Education Course Syllabus, AAAI Meeting, Mar. 5, 1991.
Schad, V. et al. (1991) "The Potential Use of T Cell Epitopes to alter the Immune Response" *Immunology* 3:217–224.
Stewart, et al. (1987) "Immunogenicity and Tolerogenicity of a Major House Dust Mite Allergen, Der p I from *Dermatophagoides pteronyssinus*, in Mice and Rats" Int. Arch. Allergy App. Immunol. 83(1):44–51.

(List continued on next page.)

*Primary Examiner*—Laurie Scheiner
*Attorney, Agent, or Firm*—Lahive & Cockfield, LLP

[57] ABSTRACT

The present invention features isolated DNA encoding allergens of Dermatophagoides (house dust mites) particularly of the species *Dermatophagoides farinae* and *Dermatophagoides pteronyssinus*, which are protein allergens or peptides which include at least one epitope of the protein allergen. In particular, the invention provides DNA encoding the major *D. farinae* allergens, *Der f* I and *Der f* II and DNA encoding the major *D. pteronvssinus* allergens, *Der p* I and *Der p* II. The present invention further relates to proteins and peptides encoded by the isolated *D. farinae* and *D. pteronvssinus* DNA, including proteins containing sequence polymorphisms. In addition, the proteins or peptides encoded by the isolated DNA, their use a diagnostic and therapeutic reagents and methods of diagnosing and treating sensitivity to house dust mite allergens, are disclosed.

5 Claims, 29 Drawing Sheets

OTHER PUBLICATIONS

Stewart, et al. (1987) "In vitro translation of Messenger RNA from the House Dust Mite" *Int. Archs. Allergy Apl. Immunol.*, 83:384:389.

Stewart, et al. (1987) An Allergen and Antigenic Mapping Analysis of a Major Mite Allergen, Der p I: Apr. 11–12, 1988, DPC First International Symposium, Laguna Niguel, California.

Stewart, et al (1987) [Abstracts from the Annual Metting], "The Physico–chemical Characterization of a Major Protein Allergen Der–P–I from the House Dust, *Dermatophagoides pteronyssinus* Amino Acid Analysis and Circular Dichroism Studies" *Int Arch Allergy Appl. Immunol* 82:(3–4) (Conference Paper).

Stewart, et al, "2. Epitope mapping analysis of the major mite allergens using synthetic peptides" Meeting on Sep. 1987, (see International Workshop Report, 1988) Mite Allergy conference, Bad Kreuznach.

Thomas, et al. (1988) "Cloning and Expression of DNA Coding for the Major House Dust Mite Allergen Der p I in *Escherichia Coli*" *Int. Archs. Allergy Appl. immun.* 85:127–129.

Thomas et al. "4. Expression of the house dust mite allergen Der p I in *E. coli*" Mite Allergy conference, BadKreuznach.

Tasieda. et al. "Isolation and Characterization of two allergens from *Dermatophagoides farinae*" *Chemical Abstracts*, 105:552 (abstract).

Thomas, et al., (1990) "Anlalysis and Expression of cDNA clones coding for house dust mite allergens" *Biochem. Genetics*, 113:179.

Thomas et al. "6. recombinant Mite Allergens", Proc. of Workshop XIV London Europe Acad. Allergy, Sep. 1989.

Tovey, et al. (1989) "Cloning and Sequencing of a cDNA Expressing a Recombinant House Dust Mite Protein that binds human IgE and corresponds to an important low molecular weight allergen" Brief Definition, J. of Exp. Med. 170(4):1457–62.

Trudinger, et al. (1991) "cDNA endocing the major mite allergen Der f II," *Clinical and Exper. Allergy* 24:33–37.

Van't Hof, et al. (1991) "Epitope Mapping of the *dermatophagoides pteronyssinus* house dust mite major allergen Der p II using overlapping synthetic peptides" *Molecular Immunology*, 28(11):1225–1232.

Yssel, et al. (1992) "T cell activation–inducing epitopes of the hous dust mite allergen Der p I" *J. of Immunology* 148:738–745.

Yssel, et al., "T Cell Activation by allergen derived synthetic peptides" Session 4: Immunity to Peptides, Sep. 24, 1990, Trinity College.

Yukki, et al. (1990) "Cloning and Sequencing of cDNA Corresponding to mite major allergen Der f II" *Jpn. J. Allergoi*, 39(6):557–561.

```
-23
AAA AAC CGA TTT TTG ATG AGT GCA GAA GCT TTT GAA CAC CTC AAA ACT        48
Lys Asn Arg Phe Leu Met Ser Ala Glu Ala Phe Glu His Leu Lys Thr
                            -1  1                  -10

CAA TTC GAT TTG AAT GCT GAA ACT AAC GCC TGC AGT ATC AAT GGA AAT        96
Gln Phe Asp Leu Asn Ala Glu Thr Asn Ala Cys Ser Ile Asn Gly Asn
 10                                      20

GCT CCA GCT GPA ATC GAT TTG CGA CAA ATG CGA ACT GTC ACT CCC ATT       144
Ala Pro Ala Glu Ile Asp Leu Arg Gln Met Arg Thr Val Thr Pro Ile
         30                                              40

CGT ATG CAA GGA GGC TGT GGT TCA GGT TCT TTC TCT GGT GTT GCC           192
Arg Met Gln Gly Gly Cys Gly Ser Gly Ser Phe Ala Ser Gly Val Ala

GCA ACT GAA TCA GCT TAT TTG GCT CAC CGT AAT CAA Gln TCA GAT CTT       240
Ala Thr Glu Ser Ala Tyr Leu Ala His Arg Asn Asn Gln Ser Asp Leu
         60                                      70

GCT GAA CAA CAA GAA TTA GTC GAT TGT GCT TCC CAA CAC CAC TGT CAT GGT   288
Ala Glu Gln Gln Glu Leu Val Asp Cys Ala Ser Gln His His Cys His Gly
                         80

GAT ACC ATT CCA CGT GGT ATT GAA TAC ATC CAA CAT CAA GGT GTC GTC       336
Asp Thr Ile Pro Arg Gly Ile Glu Tyr Ile Gln His Asn Gly Val Val
 90                                              100

CAA GAA AGC TAC TAT CGA TAC GTT GCA CGA TCA GAA TGC CGA CGA           384
Gln Glu Ser Tyr Tyr Arg Tyr Val Ala Arg Glu Gln Ser Cys Arg Arg
             110                                          120

CCA AAT GCA CAA CGT TTC GGT ATC TCA AAC TAT TGC CAA ATT TAC CCA       432
Pro Asn Ala Gln Arg Phe Gly Ile Ser Asn Tyr Cys Gln Ile Tyr Pro
                     130
```

Fig. 1A

```
CCA AAT GCA AAC AAA ATT CGT GAA GCT TTG GCT CAA ACC CAC AGC GCT    480
Pro Asn Ala Asn Lys Ile Arg Glu Ala Leu Ala Gln Thr His Ser Ala
        140                                     150

ATT GCC GTC ATT ATT GGC ATC AAA GAT TTA GAC TTC CGT CAT TAT        528
Ile Ala Val Ile Ile Gly Ile Lys Asp Leu Asp Phe Arg His Tyr
                    160

GAT GGC CGA ACA ATC ATT CAA CGC GAT AAT GGT TAC CAA CCA AAC TAT    576
Asp Gly Arg Thr Ile Ile Gln Arg Asp Asn Gly Tyr Gln Pro Asn Tyr
170                                         180

CAC GCT GTC AAC ATT GTT AAC GCA CAA GGT GTC GAT GTC TAT            624
His Ala Val Asn Ile Val Tyr Ser Asn Ala Gln Gly Val Asp Tyr
            190                                         200

TGG ATC GTA CGA AAC AGT TGG GAT ACC AAT TGG GGT GAT AAT GGT TAC    672
Trp Ile Val Arg Asn Ser Trp Asp Thr Asn Trp Gly Asp Asn Gly Tyr
                        210

GGT TAT TTT GCT GCC AAC ATC GAT TTG ATG ATT GAA GAA TAT CCA        720
Gly Tyr Phe Ala Ala Asn Ile Asp Leu Met Met Ile Glu Glu Tyr Pro
220             222

TAT GTT GTC ATT CTC TAAACAAAAAGACAATTTCTTATATGATTGTCACTAATTTATT    778
Tyr Val Val Ile Leu

TAAATCAAAATTTTTAGAAAATGAATAAATTCATTCACAAAAATTAAAAAAAAAAAAAAAA    841
AAAAAAAAAAA 857
```

Fig. 1B

```
            1                                  10
Der p 1  Thr Asn Ala Cys Ser Ile Asn - Gly Asn Ala Pro
              *       *       *       *           *
Der f 1  Thr Ser Ala Cys Arg Ile Asn Ser Val Asn Val Pro

20
Der p 1  Ala Glu Ile Asp Leu Arg Gln Met
              *       *       *
Der f 1  Ser Glu Leu Asp Leu Arg Ser Leu
```

Fig. 3

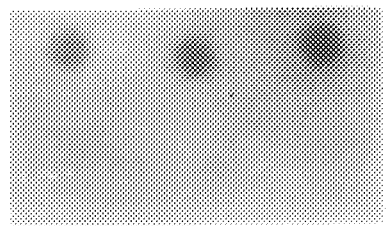 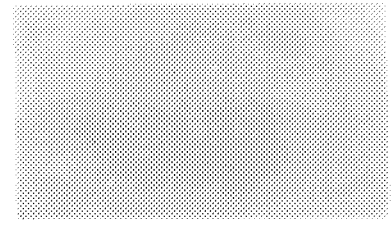
FIG. 4

```
                                                                                        -16
CACAAATTCTTCTTCTTCCTTACTACTGATCATTAATCTGAAAACAAAACCAAACAAACCAT

-10                                           -1  1
TCAAAATGATG TAC AAA ATT TTG TGT CTT TCA TTG TTG GTC GCA GCC GTT
            Met Tyr Lys Ile Leu Cys Leu Ser Leu Leu Val Ala Ala Val

10
GCT CGT GAT CAA GTC GAT GTC AAA GAT TGT GCC AAT CAT GAA ATC AAA
Ala Arg Asp Gln Val Asp Val Lys Asp Cys Ala Asn His Glu Ile Lys 20                                  30
AAA GTT TTG GTA CCA GGA TGC CAT GGT TCA GAA CCA TGT ATC ATT CAT
Lys Val Leu Val Pro Gly Cys His Gly Ser Glu Pro Cys Ile Ile His

40
CGT GGT AAA CCA TTC CAA TTG GAA GCC GTT TTC GAA GCC AAC CAA AAC
Arg Gly Lys Pro Phe Gln Leu Glu Ala Val Phe Glu Ala Asn Gln Asn 50                                          60
ACA AAA ACG GCT AAA ATT GAA ATC AAA GCC TCA ATC GAT GGT TTA GAA
Thr Lys Thr Ala Lys Ile Glu Ile Lys Ala Ser Ile Asp Gly Leu Glu
```

Fig. 7A

```
GTT GAT GTT CCC GGT ATC GAT CCA AAT GCA TGC CAT TAC ATG AAA TGC
Val Asp Val Pro Gly Ile Asp Pro Asn Ala Cys His Tyr Met Lys Cys
                      70                      90

CCA TTG GTT AAA GGA CAA CAA TAT GAT ATT AAA TAT ACA TGG AAT GTT
Pro Leu Val Lys Gly Gln Gln Tyr Asp Ile Lys Tyr Thr Trp Asn Val
        80                     100                          110

CCG AAA ATT GCA CCA AAA TCT GAA AAT GTT GTC ACT GTT AAA GTT
Pro Lys Ile Ala Pro Lys Ser Glu Asn Val Val Thr Val Lys Val
                                    120

ATG GGT GAT GAT GGT GTT TTG GCC TGT GCT ATT GCT ACT CAT GCT AAA
Met Gly Asp Asp Gly Val Leu Ala Cys Ala Ile Ala Thr His Ala Lys

ATC CGC GAT TAAATCAAACAAAATTTATTGATTTTGTAATCACAAATGATTGATTTTCTT
Ile Arg Asp
        129

TCCAAAAAAAAATAAATAAAATTTTGGGAATTC  581
```

Fig. 7B

Der p II   DQVDVKDCANHEIKKVLVPGCHGSEPCIIHRGKPF

*      * *       *

Der f II   DQVDVKD?ANNEIKKVMVDG?HGSDP?IIHRGKPF

\* = NON HOMOLOGOUS RESIDUES.

```
GAATTCCGTTTTCTTCCATCAAAATTAAAAATTCATCAAAA                                              
        -90                                       -98                                  
                                                  ATG AAA TTC GTT TTG GCC ATT      62
                                                  Met Lys Phe Val Leu Ala Ile
                                                  -80
GCC TCT TTG GTA TTG AGC ACT GTT TAT GCT CGT CCA GCT TCA ATC AAA ACT                    116
Ala Ser Leu Val Leu Ser Thr Val Tyr Ala Arg Pro Ala Ser Ile Lys Thr
            -70                              -60
TTT GAA GAA TTC AAA AAA TTC AAC GCC TTC AAC AAA TAT GCC ACC GTT GAA GAG GAA            170
Phe Glu Glu Phe Lys Lys Phe Asn Ala Phe Asn Lys Tyr Ala Thr Val Glu Glu Glu
                -50                                              -40
GAA GTT GCC CGT AAA AAC TTT TTG AAA TCA TTG AAA TAT GTT GAA GCT AAC AAA                224
Glu Val Ala Arg Lys Asn Phe Leu Lys Ser Leu Lys Tyr Val Glu Ala Asn Lys
                                -30                                          -20
GGT GCC ATC AAC CAT TTG TCC GAT TTG TCA GAT CTC TTT GAA CAA CTC AAA AAC CGT TAT        278
Gly Ala Ile Asn His Leu Ser Asp Leu Ser Asp Leu Phe Glu Gln Leu Lys Asn Arg Tyr
                                            -10
TTG ATG AGT GCT GAA GCT TTT GAA CAA CTC ACT AAA CTC CAA TTC GAT TTG AAT GCC            332
Leu Met Ser Ala Glu Ala Phe Glu Gln Leu Thr Lys Leu Gln Phe Asp Leu Asn Ala
-1  ↑                                          10
GAA ACA AGC GCT TGC CGT ATC AAT TCG GTT AAC GTT CCA TCG GAA TTG GAT TTA                386
Glu Thr Ser Ala Cys Arg Ile Asn Ser Val Asn Val Pro Ser Glu Leu Asp Leu
                20                                          30
CGA TCA CTG CGA ACT GTC ACT CCA ACT ATC CGT ATG CAA GGA GGC TGT TGT GGT TCA TGT        440
Arg Ser Leu Arg Thr Val Thr Pro Thr Ile Arg Met Gln Gly Gly Cys Cys Gly Ser Cys
                    40
TGG GCT TTC TCT GGT GTT GCC GCA ACT GAA TCA GCT TAT TTG GCC TAC CGT AAC                494
Trp Ala Phe Ser Gly Val Ala Ala Thr Glu Ser Ala Tyr Leu Ala Tyr Arg Asn
                                                                50
```

| | | | | | | | | | | |
|---|---|---|---|---|---|---|---|---|---|---|
| ACG | TCT | TTG | GAT | CTT | TCT | GAA | CAG | GAA | CTC | GTC | GAT | TGC | GCA | TCT | CAA | CAC | GGA | 548 |
| Thr | Ser | Leu | Asp | Leu | Ser | Glu | Gln | Glu | Leu | Val | Asp | Cys | Ala | Ser | Gln | His | Gly | |
| | | | | 60 | | | | 80 | | | | | | | | 70 | | |

TGT CAC GGC GAT ACA ATA CCA AGA GGC GAA ATC GAA CAA AAT GGT GTC  602
Cys His Gly Asp Thr Ile Pro Arg Gly Ile Glu Tyr Ile Gln Asn Gly Val
 90                                         100

GTT GAA AGA AGC TAT CCA TAC GTT GCA CGA GAA CGA TGC CGA CGA CCA  656
Val Glu Arg Ser Tyr Pro Tyr Val Ala Arg Glu Gln Arg Cys Arg Arg Pro
    110                                     120

AAT TCG CAA CAT TAC GGT ATC TCA AAC TAC TGC CAA ATT TAT CCA GAT GTG  710
Asn Ser Gln His Tyr Gly Ile Ser Asn Tyr Cys Gln Ile Tyr Pro Asp Val
         130                                     140

AAA ATC CGT GAA GCT TTG ACT CAA ACA CAC ATT GCC GTC ATT ATT  764
Lys Ile Arg Glu Ala Leu Thr Gln Thr His Ile Ala Val Ile Ile
         150                                     160

GGC AAA GAT TTG AGA GCT TTC CAA TAT CAT TAT GAT GGA CGA ATT CAA  818
Gly Lys Asp Leu Arg Ala Phe Gln Tyr His Tyr Asp Gly Arg Ile Gln
             170

CAT GAC AAT GGT TAT CAA CCA AAC TAT CAT TAT GCC AAC ATT GTC GGT TAC GGA  872
His Asp Asn Gly Tyr Gln Pro Asn Tyr His Ala Val Asn Ile Val Gly Tyr Gly
 180                                     190

AGT ACA CAA GGC GAC GAT TAT TGG CGA AAC AGT TGG GAT ACT ACC TGG  926
Ser Thr Gln Gly Asp Asp Tyr Trp Arg Asn Ser Trp Asp Thr Thr Trp
        200                                     210

GGA GAT AGC GGA TAC TAT TTC CAA GCC GGA AAC CTC ATG ATG ATC GAA  980
Gly Asp Ser Gly Tyr Tyr Phe Gln Ala Gly Asn Leu Met Met Ile Glu
        220       223

CAA TAT CCA TAT GTT GTA ATC ATG TGAACATTTGAAATTGAATATATTTATTTGTTTCAAAAT  1044
Gln Tyr Pro Tyr Val Val Ile Met
AAAAACAACTACTCTTGCGAGTATTTTTTACTCGGAATTC 1084

Fig. 10B

```
                 10        20        30        40        50        60
Der p  1   TNACSING*NAPAEIDLRQMRTVTPIRMQGGCGSCWAFSGVAATESAYLAHRNQSLDLAEQE
Der f  1   .S..R..SV.V.S.L...SL..................Y..T.....S...
                                       ▲▲▲
                                     ▲
                 70        80        90       100       110       120
Der p  1   LVDCASQHGCHGDTIPRGIEYIQHNGVVQESYYRYVAREQSCRRPNAQRFGISNYCQIYPPN
Der f  1   ..............Q.....E.RS.P......R......S.HY..........D 130       140       150       160       170       180
Der p  1   ANKIREALAQTHSAIAVIIGIKDLDAFRHYDGRTIIQRDNGYQPNYHAVNIVGYSNAQGVDY
Der f  1   VKQ.....T..T..........R..Q.........H...........GST...D..
                                                      ▲

190       200       210       220
Der p  1   WIVRNSWDTNWGDNGYGYFAANIDLMMIEEYPYVVIL
Der f  1   ........T...S.....Q.GNN......Q......M
           ▲▲▲
```

Fig. 11

```
Cathepsin H   MWTALPLLCAGAWLLSAGATA------------------------------------ELTY-NA-IEKFH---FTSWMKQHQKTY-SS-
Cathepsin L            MTPLLLAVLCLGTALA------------------------------------------TPKFDQ-TF-NAQWH-----QWKSTHRRLY-GT-
Papain         MAMIPSISKLLFVAICLFVYMGLSFG-----------------------DFSIVGYSQNDLTS-TE-RLIQL---FESWMLKHNKIYKNI-
Aleurain       MAHARVLLALAVLATAAVAYASSSSFADSNPIRPVTDRAASTLESAVLGALGRTRHALRFARFAVRYGKSYESA-
CP1                          MKVILLFVLAVFTVF-----------------------------VSSRGIPPEEQ-SQ-FLEFQ---DKFNKKYSHEEY-LE-
CP2                       MRLLVFLILLIFVNFSFA----------------------------NVRPNGRRFS-ES-QYRTA---FTEWTLKFNRQY-SS-
Cathepsin B               MWWSLIPLSCLLALTSA----------------------------------------------HDK---PS-
CTLA-2μ        MVSICEQKLQHFSAVFLLILCLGMMSA--------------------APPPDPSLDNEWKEWKTKFAKAYNLN-
CTLA-2b        MVSICEQKLQHFSAVFLLILCLGMMSA--------------------APSPDPSLDNEWKEWKTTFAKAYSLD-
MCP               NLLLAVLCLGTALA------------------------------------------TPKFDQTFSAEWHQWKSTHRRLY-GT-
Der f I                MKFVLAIASLLVLSTVYA------------------------------------------RPASIKTFEEFKKAFNKNYATVE
                                                                                      **     *     *
```

Fig. 12A

```
Cathepsin H    REYSHRLQVFANNWRKIQAHN--QRN--HTFKMG--LNQFSDMSFAEIKIKYL-WSE-PQNCS--AT-KS--NYL--RGTGP
Cathepsin L    NEEEWRRAVWEKNMRMIQIHNGEYSNGKHGFIHE--MNAFGDMTNEEFRQIVN-GYR-HQKHK--KG-RL--FQE--PLMLQ
Papain         DEKIYRFEIFKDNLKYIDETN--KKN--NSYWLG--LNVFADMSNDEFKEKYT-GSI-AGNYT--TTELSYEEVL-NDGDVN
Aleurain       AEVRRRFRIFSESLEEVRSTN--RKG--LPYRLG--INRFSDMSWEEFQATRL-GA--AQTCS--ATLAG--NHL-MRDAAA
CP1            RFEIFKSNLGKIEELNLIAIN--HKA--DT-KFG--VNKFADLSSDEFKNYYLNNKEAIFTDD--LP-VA--DYLDDEFINS
CP2            SEFSNRYSIFKSNMDYVDNWN-SKGD--SQTVLG--LNNFADITNEEYRKTYL-GTR-VNAHSYNGYDGR--EVLNVEDLQT
Cathepsin B    ---FHPLS---DDM--INYIN--KQN--TTWQAG--RN-EYNV-DISYLKKPC-GTV-LGGPK--LP-ER--VGF--SEDIN
CTLA-2μ        NEERHRRLVWEENKKKIEAHNADYEQGKTSFYMG--LNQFSDLTPEEFKTNCY-GNSLNRGEM
CTLA-2b        DEERHRRLMWEENKKKIEAHNADYERGKTSFYMG--LNQFSDLTPEEFRTNCC-GSSMCRGEM
MCP            NEEEWRRAIWEKNMRMIQLHNGEYSNGQHGFSME--MNAFGDMTNEEFRQVVN-GYRHQKHKK
Der p I                       --KNRFL-MS-AEAFEH-L-KTQFRLNAE
Actinidin           LRFIDEHNAD-TNR--SYKVG--LNQFADLTGEEFRSTYL-G
Der f I        EEEVARKN-FLESLKYVEA-NKGAINHLSDLSLDEFKNRYL-MS-AEAFEQ-L-KTQFDLNAE
               **  *   *          *    *    *       ****..  **     *
               *   *            *        *          **      *      *
```

Fig. 12B

```
GAT CAA GTC GAT GTT AAA GAT TGT GCC AAT GAA ATC AAA AAA GTA ATG        51
Asp Gln Val Asp Val Lys Asp Cys Ala Asn Glu Ile Lys Lys Val Met
                20                          10

GTC GAT GGT TGC CAT GGT TCT GAT CCA TGC ATC ATC CAT CGT GGT AAA CCA   102
Val Asp Gly Cys His Gly Ser Asp Pro Cys Ile Ile His Arg Gly Lys Pro
                                        30

TTC ACT TTG GAA GCC TTA TTC GAT GCC AAC CAA AAC ACT AAA ACC GCT AAA   153
Phe Thr Leu Glu Ala Leu Phe Asp Ala Asn Gln Asn Thr Lys Thr Ala Lys
                        40                                  50

ACT GAA ATC AAA GCC AGC CTC GAT GGT CTT GAA ATT CCC GGT ATT          204
Thr Glu Ile Lys Ala Ser Leu Asp Gly Leu Glu Ile Pro Gly Ile

GAT ACC AAT GCT TGC CAT TTT ATG AAA TGT CCA TTG GTT AAA GGT CAA CAA   255
Asp Thr Asn Ala Cys His Phe Met Lys Cys Pro Leu Val Lys Gly Gln Gln
        70                                  80

TAT GAT GCC AAA TAT ACA TGG AAT ACA GTC AAA ATT GCA CCA AAA TCT GAA   306
Tyr Asp Ala Lys Tyr Thr Trp Asn Thr Val Lys Ile Ala Pro Lys Ser Glu
                90                                          100

AAC GTT GTC GTT ACA GTC AAA CTT GTT GGT GAT AAT GGT GTT TTG GCT TGC  357
Asn Val Val Val Thr Val Lys Leu Val Gly Asp Asn Gly Val Leu Ala Cys
                            110

GCT ATT GCT ACC CAC GCT AAA ATC CGT GAT TAAAAAAAAAAATAAATATGAAAATT   414
Ala Ile Ala Thr His Ala Lys Ile Arg Asp
120                                     129

TTCACCAACATCGAACAAAATTCAATAACCAAAATTTGAATCAAAAAACGGAATTCCAAGCTGAGCGC  481

CGGTCGCTAC                                                            491
```

Fig. 14

```
Dp II:  CACAAATTCTTCTTTCTTCCTTACTACTGATCATTAATCTGAAAACAAACCAAACAAACCAT              63
                           -16

Dp II:  TCAAAAATGATG TAC AAA ATT TTG TGT CTT TCA TTG GTC GCA GCC GTT           113
                 Met Tyr Lys Ile Leu Cys Leu Ser Leu Val Ala Ala Val
                  -1  1                                -10

Dp II:  GCT CGT GAT CAA GTC GAT GTC AAA GAT TGT GCC AAT CAT GAA ATC AAA       161
        Ala Arg Asp Gln Val Asp Val Lys Asp Cys Ala Asn His Glu Ile Lys

Df II:  ... ... ... ... ..T ... ... ... ... ... ..C A.. ... ... ... ...        42
                                                      Asn
                                    20                          30

Dp II:  AAA GTT TTG GTA CCA GGA TGC CAT GGT TCA GAA CCA TGT ATC ATT CAT       209
        Lys Val Leu Val Pro Gly Cys His Gly Ser Glu Pro Cys Ile Ile His

Df II:  ... ..A A.. ..C GAT ...T ... ... ... ... ... ..T ... ..C ... ...      90
                        Met                     Asp
                                                          40

Dp II:  CGT GGT AAA CCA TTC CAA TTG GAA GCC GTT TTC GAA GCC AAC CAA AAC       257
        Arg Gly Lys Pro Phe Gln Leu Glu Ala Val Phe Glu Ala Asn Gln Asn

Df II:  ... ... ... ... ACT ... ... ... ... ... T.A ... ..T ... ... ...      138
                        Thr                     Leu     Asp
```

Fig. 16A

```
Dp II:  ACA AAA ACG GCT AAA ATT GAA ATC AAA GCC TCA ATC GAT GGT TTA GAA   305
        Thr Lys Thr Ala Lys Ile Glu Ile Lys Ala Ser Ile Asp Gly Leu Glu
                         50                  60
Df II:  ..T ... ... ..C ... ..C. ... ... ... ... AGC C.. ... ... C.T ...   186
                              Thr                Leu

Dp II:  GTT GAT GTT CCC GGT ATC GAT CCA AAT GCA TGC CAT TAC ATG AAA TGC   353
        Val Asp Val Pro Gly Ile Asp Pro Asn Ala Cys His Tyr Met Lys Cys
                              70
Df II:  A.. ... ... ... ... ..T ... A.C ... ..T ... ... .TT ... ... ..T   234
        Ile                          Thr                    Phe
         80

Dp II:  CCA TTG GTT AAA GGA CAA CAA TAT GAT ATT AAA TAT ACA TGG AAT GTT   401
        Pro Leu Val Lys Gly Gln Gln Tyr Asp Ile Lys Tyr Thr Trp Asn Val
                                              90
Df II:  ... ... ... ... ... ..T ... ... ... ... ... ... ... ... ..G ...   282
                                              GCC
                                              Ala

Dp II:  CCG AAA ATT GCA CCA AAA TCT GAA AAT GTT GCA CCA ACT GTT AAA GTT   449
        Pro Lys Ile Ala Pro Lys Ser Glu Asn Val Val Val Thr Val Lys Val
                         100                                  110
Df II:  ... ... ... ... ... ... ... ... ... ..C ... ..T ...A ..C ... C..   330
                                                                      Leu
```

Fig. 16B

```
Dp II:  ATG GGT GAT GAT GGT GTT TTG GCC TGT GCT ATT GCT ACT CAT GCT AAA  497
        Met Gly Asp Asp Gly Val Leu Ala Cys Ala Ile Ala Thr His Ala Lys
                                    120

Df II:  G.T ... ... A.. ... ... ... ..T ... ..C ... ..C ... ... ... ...  378
        Val                                     Asn

Dp II:  ATC CGC GAT TAA ATCAAACAAAATTTATTGATTTTGTAATCACAAATGATTGATTTTCTT  557
        Ile Arg Asp END
                129

Df II:  ... ..T ... ... .AA....A....TAAATA...AAA.T.TCA.CA.C.CGAAC.AAA.TCA  438

Dp II:  TCCAAAAAAAAAATAAATAAAATTTTGGGAATTC                                591

Df II:  ATA.CC....TTTG..TC....AC____GGAATTC                               469
```

Fig. 16C

|           |    10      |    20      |    30      |    40      |    50      |    60      |
|-----------|------------|------------|------------|------------|------------|------------|
| Der p I (a) | TNACSINGNA | PAEIDLRQMR | TVTPIRMQGG | CGSCWAFSGV | AATESAYLAH | RNQSLDLAEQ |
| Der p I (b) | ---------- | ---------- | ---------- | ---------- | -------Y-- | ---------- |
| Der p I (c) | ---------- | ---------- | ---------- | ---------- | -------Y-- | ---------- |
| Der p I (d) | ---------- | ---------- | ---------- | ---------- | ---------- | ---------- |

|           |    70      |    80      |    90      |   100      |   110      |   120      |
|-----------|------------|------------|------------|------------|------------|------------|
| Der p I (a) | ELVDCASQHG | CHGDTIPRGI | EYIQHNGVVQ | ESYYRYVARE | QSCRRPNAQR | FGISNYCQIY |
| Der p I (b) | ---------- | ---------- | ---------- | ---------- | ---------- | ---------- |
| Der p I (c) | ---------- | ---------- | K--------- | ---------- | ---------- | ---------- |
| Der p I (d) | ---------- | ---------- | ---------- | ---------- | ---------- | ---------- |

|           |   130      |   140      |   150      |   160      |   170      |   180      |
|-----------|------------|------------|------------|------------|------------|------------|
| Der p I (a) | PPNANKIREA | LAQTHSAIAV | IIGIKDLDAF | RHYDGRTIIQ | RDNGYQPNYH | AVNIVGYSNA |
| Der p I (b) | ---V------ | ---------- | ---------- | ---------- | -------Y-- | ---------- |
| Der p I (c) | ---V------ | ----T----- | ---------- | ---------- | -------Y-- | ---------- |
| Der p I (d) | ---------- | ---------- | ---------- | ---------- | ---------- | ---------- |
| Der p I (e) |            |            |            |            |            |            |

|           |   190      |   200      |   210      |   220      |            |
|-----------|------------|------------|------------|------------|------------|
| Der p I (a) | QGVDYWIVRN | SWDTNWGDNG | YGYFAANIDL | MMIEEYPYVV | IL         |
| Der p I (b) | ---------- | ---------- | ---------- | ---------- | --         |
| Der p I (c) | ---------- | ---------- | ---------- | ---Q------ | --         |
| Der p I (d) | ---------- | ---------- | ---------- | ---------- | --         |
| Der p I (e) | ---------- | ---------- | ---------- | ---------- | --         |

Fig. 18

```
                    10         20         30         40         50
Der p II (c)  DQVDVKDCANHEIKKVLVPGCHGSEPCIIHRGKPFQLEAVFEANQNTKTAK
         (1)  .........H....L.P.....E..........Q...V.E....T....
         (2)  .........H....L.P.....E..........Q...V.E....S....
Der f II      ........N...M.D.......D..........T...L.D....T....

60         70         80         90        100
Der p II (c)  IEIKASIDGLEVDVPGIDPNACHYMKCPLVKGQQYDIKYTWNVPKIAPKSE
         (1)  .......I...........P...YM..................I.....
         (2)  .......I...........P...YM..................I.....
Der f II      ......L............T...FM......A...........I.....
                                         V                  I 110        120
Der p II (c)  NVVVTVKVMGDDGVLACAIATHAKIRD
         (1)  .....VM.DD........A....I..
         (2)  .....VM.ND........A....L..
Der f II      .....LV.DN........A....I..
                   I              G
```

Fig. 19

```
       10        20        30        40        50        60
pFL1   DQVDKDCANNEIKKVMVPGCHGSEPCIIHRGKPFTLEALFDANQNTKTAKIEIKASLDGLE
pFL2   .........N..................................I.I............
MT 3   .........N..................................I.T............
MT 5   (1-92)...S...................................I.I............
MT18   (1-84)...N...................................I.I............
MT16   (1-70)...N.................................T.I............

70        80        90       100       110       120      130
pFL1   IDVPGIDTNACHFVKCPLVKGQQYDIKYTWNVPKIAPKSENVVTVKLIGDNGVLACAIATHAKIRD
pFL2   ..........M..............A...................V..................
MT 3   ..........M..............A...................V..................
MT 5   ..........M..............I......................................
MT18   ..........M......................................................
```

Fig. 20

```
GAATTCCTTT TTTTTCTTT CTCTCTCTAA AATCTAAAAT CCATCCAAC ATG AAA ATT    58
                                                    Met Lys Ile
                                                    -98

GTT TTG GCC ATC GCC TCA TTG TTG GCA TTG AGC GCT GTT TAT GCT CGT    106
Thr Leu Ala Ile Ala Ser Leu Leu Ala Leu Ser Ala Val Tyr Ala Arg
-95                 -90                 -85                 -80

CCA TCG ATC AAA ACT TTT GAA GAA TAC AAA AAA GCC TTC AAC AAA        154
Pro Ser Ile Lys Thr Phe Glu Glu Tyr Lys Lys Ala Phe Asn Lys
        -75                 -70                 -65

AGT TAT GCT ACC TTC GAA GAT CAA GAA GCT GCC CGT AAA AAC CAT TTG    202
Ser Tyr Ala Thr Phe Glu Asp Gln Glu Ala Ala Arg Lys Asn His Leu
                -60                 -55                 -50

GAA TCA GTA AAA TAT GTT CAA TCA AAT GGA GGT GCC ATC ATT TTT TTG    250
Glu Ser Val Lys Tyr Val Gln Ser Asn Gly Gly Ala Ile Ile Phe Leu
        -45                 -40                 -35

TCC GAT TTG TCG TTG GAT GAA GAA GGG CTT CAA AAC CGA TTT TTT TTG    298
Ser Asp Leu Ser Leu Asp Glu Glu Gly Leu Gln Asn Arg Phe Leu Met
-30                 -25                 -20

GAA GCT TTT GAA CAC CTC AAA ACT CAA TTC GAT TTG AAT GCT GAA ACT    346
Glu Ala Phe Glu His Leu Lys Thr Gln Phe Asp Leu Asn Ala Glu Thr
-15                 -10                 -5                   -1

AAC GCC TGC AGT ATC AAT GGA AAT GCT CCA GAA ATC GAT TTG CGA        394
Asn Ala Cys Ser Ile Asn Gly Asn Ala Pro Glu Ile Asp Leu Arg
         5                  10                  15
```

Fig. 21A

```
CAA ATG CGA ACT GTC ACT CCC ATT CGT ATG CAA GGA GGC TGT GGT TCA    442
Gln Met Arg Thr Val Thr Pro Ile Arg Met Gln Gly Gly Cys Gly Ser
        20              25              30

TGT TGG GCT TTC TCT GGT GTT GCC GCA ACT GAA TCA TAT TTG GCT        490
Cys Trp Ala Phe Ser Gly Val Ala Ala Thr Glu Ser Tyr Leu Ala
    35              40              45

CAC CGT AAT CAA TCA TTG GAT CTT GCT GAA CAA GAA TTA GTC GAT TGT    538
His Arg Asn Gln Ser Leu Asp Leu Ala Glu Gln Glu Leu Val Asp Cys
50              55              60              65

GCT TCC CAA CAC GGT TGT CAT GGT GTC GTC CAA GAT ACC ATT CCA CGT ATT GAA   586
Ala Ser Gln His Gly Cys His Gly Val Val Gln Asp Thr Ile Pro Arg Ile Glu
            70              75              80

TAC ATC CAA CAT AAT GGT CGA CGA GTC CAA GAA AGC TAC TAT CGA TAC GTT      634
Tyr Ile Gln His Asn Gly Arg Arg Val Gln Glu Ser Tyr Tyr Arg Tyr Val
                85              90              95

GCA CGA GAA CAA TCA TGC CGA CGA CCA AAT GCA CAA CGT TTC GGT ATC          682
Ala Arg Glu Gln Ser Cys Arg Arg Pro Asn Ala Gln Arg Phe Gly Ile
        100             105             110

TCA AAC TAT TGC CAA ATT TAC CCA CCA AAT GCA AAC ATT CGT GAA              730
Ser Asn Tyr Cys Gln Ile Tyr Pro Pro Asn Ala Asn Ile Arg Glu
115             120             125
```

Fig. 21B

```
GCT TTG GCT CAA ACC CAC AGC GCT ATT ATT GGC ATC AAA    778
Ala Leu Ala Gln Thr His Ser Ala Ile Ile Gly Ile Lys
130                 135                 140         145

GAT TTA GAC GCA TTC CGT CAT TAT GAT GGC CGA ACA ATC ATT CAA CGC    826
Asp Leu Asp Ala Phe Arg His Tyr Asp Gly Arg Thr Ile Ile Gln Arg
                150                 155                 160

GAT AAT GGT TAC CAA CCA AAC TAT CAC GCT GTC AAC ATT GTT GGT TAC    874
Asp Asn Gly Tyr Gln Pro Asn Tyr His Ala Val Asn Ile Val Gly Tyr
            165                 170                 175

AGT AAC GCA CAA GGT GTC GAT TAT TGG ATC GTA CGA AAC AGT TGG GAT    922
Ser Asn Ala Gln Gly Val Asp Tyr Trp Ile Val Arg Asn Ser Trp Asp
        180                 185                 190

ACC AAT TGG GGT GAT AAT GGT TAC GGT TAT TTT GCT GCC AAC ATC GAT    970
Thr Asn Trp Gly Asp Asn Gly Tyr Gly Tyr Phe Ala Ala Asn Ile Asp
    195                 200                 205

TTG ATG ATG ATT GAA GAA TAT CCA TAT GTT GTC ATT CTC TAAACAAAAA    1019
Leu Met Met Ile Glu Glu Tyr Pro Tyr Val Val Ile Leu
210                 215                 220

GACAATTTCT TATATGATTG TCACTAATTT ATTTAAAATC AAAATTTTTA GAAAATGAAT    1079

AAATTCATTC ACAAAAATTA AAAAAAAAAA AAAAAAAAAA AAAAAAAAAA AAAAAAAAAA    1139

AAAAAAAAAA AAAAAAAAAA AAAAAAAAAA AAA    1172
```

Fig. 21C

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 834 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..738

( x i ) SEQUENCE DESCRIPTION: SEQ ID NO:1:

```
AAA  AAC  CGA  TTT  TTG  ATG  AGT  GCA  GAA  GCT  TTT  GAA  CAC  CTC  AAA  ACT          48
Lys  Asn  Arg  Phe  Leu  Met  Ser  Ala  Glu  Ala  Phe  Glu  His  Leu  Lys  Thr
-23            -20                      -15                      -10

CAA  TTC  GAT  TTG  AAT  GCT  GAA  ACT  AAC  GCC  TGC  AGT  ATC  AAT  GGA  AAT          96
Gln  Phe  Asp  Leu  Asn  Ala  Glu  Thr  Asn  Ala  Cys  Ser  Ile  Asn  Gly  Asn
          -5                      -1   1                 5

GCT  CCA  GCT  GAA  ATC  GAT  TTG  CGA  CAA  ATG  CGA  ACT  GTC  ACT  CCC  ATT         144
Ala  Pro  Ala  Glu  Ile  Asp  Leu  Arg  Gln  Met  Arg  Thr  Val  Thr  Pro  Ile
10                       15                      20                      25

CGT  ATG  CAA  GGA  GGC  TGT  GGT  TCA  TGT  TGG  GCT  TTC  TCT  GGT  GTT  GCC         192
Arg  Met  Gln  Gly  Gly  Cys  Gly  Ser  Cys  Trp  Ala  Phe  Ser  Gly  Val  Ala
                    30                        35                       40

GCA  ACT  GAA  TCA  GCT  TAT  TTG  GCT  CAC  CGT  AAT  CAA  TCA  TTG  GAT  CTT         240
Ala  Thr  Glu  Ser  Ala  Tyr  Leu  Ala  His  Arg  Asn  Gln  Ser  Leu  Asp  Leu
```

|     |     |     |     |     |     |     |     |     |     |     |     |     |     |     |     |
|---|---|---|---|---|---|---|---|---|---|---|---|---|---|---|---|
| GCT | GAA | CAA | GAA | TTA | GTC | GAT | TGT | GCT | TCC | CAA | CAC | GGT | TGT | CAT | GGT | 288
| Ala | Glu | Gln | Glu | Leu | Val | Asp | Cys | Ala | Ser | Gln | His | Gly | Cys | His | Gly |
|     |     |     | 60  |     |     |     | 65  |     |     |     | 70  |     |     |     |     |
| GAT | ACC | ATT | CCA | CGT | GGT | ATT | GAA | TAC | ATC | CAA | CAT | AAT | GGT | GTC | GTC | 336
| Asp | Thr | Ile | Pro | Arg | Gly | Ile | Glu | Tyr | Ile | Gln | His | Asn | Gly | Val | Val |
|     |     | 75  |     |     |     |     | 80  |     |     |     |     | 85  |     |     |     |
| CAA | GAA | AGC | TAC | TAT | CGA | TAC | GTT | GCA | CGA | GAA | CAA | TCA | TGC | CGA | CGA | 384
| Gln | Glu | Ser | Tyr | Tyr | Arg | Tyr | Val | Ala | Arg | Glu | Gln | Ser | Cys | Arg | Arg |
| 90  |     |     |     |     | 95  |     |     |     |     | 100 |     |     |     |     | 105 |
| CCA | AAT | GCA | CAA | CGT | TTC | GGT | ATC | TCA | AAC | TAT | TGC | CAA | ATT | TAC | CCA | 432
| Pro | Asn | Ala | Gln | Arg | Phe | Gly | Ile | Ser | Asn | Tyr | Cys | Gln | Ile | Tyr | Pro |
|     |     |     |     | 110 |     |     |     |     |     | 115 |     |     |     | 120 |     |
| CCA | AAT | GCA | AAC | AAA | ATT | CGT | GAA | GCT | TTG | GCT | CAA | ACC | CAC | AGC | GCT | 480
| Pro | Asn | Ala | Asn | Lys | Ile | Arg | Glu | Ala | Leu | Ala | Gln | Thr | His | Ser | Ala |
|     |     |     | 125 |     |     |     |     |     | 130 |     |     |     |     | 135 |     |
| ATT | GCC | GTC | ATT | ATT | GGC | ATC | AAA | GAT | TTA | GAC | GCA | TTC | CGT | CAT | TAT | 528
| Ile | Ala | Val | Ile | Ile | Gly | Ile | Lys | Asp | Leu | Asp | Ala | Phe | Arg | His | Tyr |
|     |     |     | 140 |     |     |     |     | 145 |     |     |     |     |     | 150 |     |
| GAT | GGC | CGA | ACA | ATC | ATT | CAA | CGC | GAT | AAT | GGT | TAC | CAA | CCA | AAC | TAT | 576
| Asp | Gly | Arg | Thr | Ile | Ile | Gln | Arg | Asp | Asn | Gly | Tyr | Gln | Pro | Asn | Tyr |
|     |     | 155 |     |     |     |     | 160 |     |     |     |     |     | 165 |     |     |
| CAC | GCT | GTC | AAC | ATT | GTT | GGT | TAC | AGT | AAC | GCA | CAA | GGT | GTC | GAT | TAT | 624
| His | Ala | Val | Asn | Ile | Val | Gly | Tyr | Ser | Asn | Ala | Gln | Gly | Val | Asp | Tyr |
| 170 |     |     |     |     | 175 |     |     |     |     | 180 |     |     |     |     | 185 |
| TGG | ATC | GTA | CGA | AAC | AGT | TGG | GAT | ACC | AAT | TGG | GGT | GAT | AAT | GGT | TAC | 672
| Trp | Ile | Val | Arg | Asn | Ser | Trp | Asp | Thr | Asn | Trp | Gly | Asp | Asn | Gly | Tyr |
|     |     |     |     | 190 |     |     |     |     | 195 |     |     |     |     | 200 |     |
| GGT | TAT | TTT | GCT | GCC | AAC | ATC | GAT | TTG | ATG | ATG | ATT | GAA | GAA | TAT | CCA | 720
| Gly | Tyr | Phe | Ala | Ala | Asn | Ile | Asp | Leu | Met | Met | Ile | Glu | Glu | Tyr | Pro |
|     |     |     | 205 |     |     |     |     |     | 210 |     |     |     |     | 215 |     |
| TAT | GTT | GTC | ATT | CTC | TAAACAAAAA | GACAATTTCT | TATATGATTG | TCACTAATTT |     |     |     |     |     |     |     | 775
| Tyr | Val | Val | Ile | Leu |     |     |     |     |     |     |     |     |     |     |     |
|     |     |     | 220 |     |     |     |     |     |     |     |     |     |     |     |     |

ATTTAAAATC AAAATTTTTT AGAAAATGAA TAAATTCATT CACAAAAATT AAAAAAAA    834

( 2 ) INFORMATION FOR SEQ ID NO:2:

( i ) SEQUENCE CHARACTERISTICS:
        ( A ) LENGTH: 245 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

|     |     |     |     |     |     |     |     |     |     |     |     |     |     |
|---|---|---|---|---|---|---|---|---|---|---|---|---|---|
| Lys | Asn | Arg | Phe | Leu | Met | Ser | Ala | Glu | Ala | Phe | Glu | His | Leu | Lys | Thr |
| -23 |     |     | -20 |     |     |     |     | -15 |     |     |     |     | -10 |     |     |
| Gln | Phe | Asp | Leu | Asn | Ala | Glu | Thr | Asn | Ala | Cys | Ser | Ile | Asn | Gly | Asn |
|     |     |     | -5  |     |     |     | -1  | 1   |     |     |     | 5   |     |     |     |
| Ala | Pro | Ala | Glu | Ile | Asp | Leu | Arg | Gln | Met | Arg | Thr | Val | Thr | Pro | Ile |
| 10  |     |     |     |     | 15  |     |     |     |     | 20  |     |     |     |     | 25  |
| Arg | Met | Gln | Gly | Gly | Cys | Gly | Ser | Cys | Trp | Ala | Phe | Ser | Gly | Val | Ala |
|     |     |     |     | 30  |     |     |     |     | 35  |     |     |     |     | 40  |     |
| Ala | Thr | Glu | Ser | Ala | Tyr | Leu | Ala | His | Arg | Asn | Gln | Ser | Leu | Asp | Leu |
|     |     |     |     | 45  |     |     |     |     | 50  |     |     |     |     | 55  |     |
| Ala | Glu | Gln | Glu | Leu | Val | Asp | Cys | Ala | Ser | Gln | His | Gly | Cys | His | Gly |
|     |     |     |     | 60  |     |     |     | 65  |     |     |     | 70  |     |     |     |
| Asp | Thr | Ile | Pro | Arg | Gly | Ile | Glu | Tyr | Ile | Gln | His | Asn | Gly | Val | Val |
|     |     | 75  |     |     |     |     | 80  |     |     |     |     | 85  |     |     |     |

```
Gln  Glu  Ser  Tyr  Tyr  Arg  Tyr  Val  Ala  Arg  Glu  Gln  Ser  Cys  Arg  Arg
 90             95                      100                      105

Pro  Asn  Ala  Gln  Arg  Phe  Gly  Ile  Ser  Asn  Tyr  Cys  Gln  Ile  Tyr  Pro
               110                      115                      120

Pro  Asn  Ala  Asn  Lys  Ile  Arg  Glu  Ala  Leu  Ala  Gln  Thr  His  Ser  Ala
               125                      130                      135

Ile  Ala  Val  Ile  Ile  Gly  Ile  Lys  Asp  Leu  Asp  Ala  Phe  Arg  His  Tyr
          140                      145                      150

Asp  Gly  Arg  Thr  Ile  Ile  Gln  Arg  Asp  Asn  Gly  Tyr  Gln  Pro  Asn  Tyr
          155                      160                      165

His  Ala  Val  Asn  Ile  Val  Gly  Tyr  Ser  Asn  Ala  Gln  Gly  Val  Asp  Tyr
170                      175                      180                      185

Trp  Ile  Val  Arg  Asn  Ser  Trp  Asp  Thr  Asn  Trp  Gly  Asp  Asn  Gly  Tyr
               190                      195                      200

Gly  Tyr  Phe  Ala  Ala  Asn  Ile  Asp  Leu  Met  Met  Ile  Glu  Glu  Tyr  Pro
               205                      210                      215

Tyr  Val  Val  Ile  Leu
               220
```

( 2 ) INFORMATION FOR SEQ ID NO:3:

( i ) SEQUENCE CHARACTERISTICS:
        ( A ) LENGTH: 588 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 69..509

( x i ) SEQUENCE DESCRIPTION: SEQ ID NO:3:

```
CACAAATTCT  TCTTTCTTCC  TTACTACTGA  TCATTAATCT  GAAAACAAAA  CCAAACAAAC         60

CATTCAAA ATG ATG TAC AAA ATT TTG TGT CTT TCA TTG TTG GTC GCA GCC              110
         Met Tyr Lys Ile Leu Cys Leu Ser Leu Leu Val Ala Ala
         -16 -15              -10                      -5

GTT GCT CGT GAT CAA GTC GAT GTC AAA GAT TGT GCC AAT CAT GAA ATC               158
Val Ala Arg Asp Gln Val Asp Val Lys Asp Cys Ala Asn His Glu Ile
        -1   1               5                    10

AAA AAA GTT TTG GTA CCA GGA TGC CAT GGT TCA GAA CCA TGT ATC ATT               206
Lys Lys Val Leu Val Pro Gly Cys His Gly Ser Glu Pro Cys Ile Ile
         15              20                  25

CAT CGT GGT AAA CCA TTC CAA TTG GAA GCC GTT TTC GAA GCC AAC CAA               254
His Arg Gly Lys Pro Phe Gln Leu Glu Ala Val Phe Glu Ala Asn Gln
 30              35                  40                      45

AAC ACA AAA ACG GCT AAA ATT GAA ATC AAA GCC TCA ATC GAT GGT TTA               302
Asn Thr Lys Thr Ala Lys Ile Glu Ile Lys Ala Ser Ile Asp Gly Leu
                 50                  55                  60

GAA GTT GAT GTT CCC GGT ATC GAT CCA AAT GCA TGC CAT TAC ATG AAA               350
Glu Val Asp Val Pro Gly Ile Asp Pro Asn Ala Cys His Tyr Met Lys
                 65                  70                  75

TGC CCA TTG GTT AAA GGA CAA CAA TAT GAT ATT AAA TAT ACA TGG AAT               398
Cys Pro Leu Val Lys Gly Gln Gln Tyr Asp Ile Lys Tyr Thr Trp Asn
         80                  85                  90

GTT CCG AAA ATT GCA CCA AAA TCT GAA AAT GTT GTC GTC ACT GTT AAA               446
Val Pro Lys Ile Ala Pro Lys Ser Glu Asn Val Val Val Thr Val Lys
     95                 100                 105

GTT ATG GGT GAT GAT GGT GTT TTG GCC TGT GCT ATT GCT ACT CAT GCT               494
```

```
Val  Met  Gly  Asp  Asp  Gly  Val  Leu  Ala  Cys  Ala  Ile  Ala  Thr  His  Ala
110            115                      120                      125

AAA  ATC  CGC  GAT  TAAATAAACA  AAATTTATTG  ATTTTGTAAT  CACAAATGAT                546
Lys  Ile  Arg  Asp

TGATTTCTT  TCCAAAAAAA  AAATAAATAA  AATTTGGGA  AT                                   588
```

( 2 ) INFORMATION FOR SEQ ID NO:4:

( i ) SEQUENCE CHARACTERISTICS:
        ( A ) LENGTH: 146 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Met  Tyr  Lys  Ile  Leu  Cys  Leu  Ser  Leu  Leu  Val  Ala  Ala  Val  Ala
-16  -15                      -10                      -5

Arg  Asp  Gln  Val  Asp  Val  Lys  Asp  Cys  Ala  Asn  His  Glu  Ile  Lys  Lys
-1    1              5                      10                       15

Val  Leu  Val  Pro  Gly  Cys  His  Gly  Ser  Glu  Pro  Cys  Ile  Ile  His  Arg
                20                      25                            30

Gly  Lys  Pro  Phe  Gln  Leu  Glu  Ala  Val  Phe  Glu  Ala  Asn  Gln  Asn  Thr
                35                      40                       45

Lys  Thr  Ala  Lys  Ile  Glu  Ile  Lys  Ala  Ser  Ile  Asp  Gly  Leu  Glu  Val
           50                      55                      60

Asp  Val  Pro  Gly  Ile  Asp  Pro  Asn  Ala  Cys  His  Tyr  Met  Lys  Cys  Pro
     65                      70                      75

Leu  Val  Lys  Gly  Gln  Gln  Tyr  Asp  Ile  Lys  Tyr  Thr  Trp  Asn  Val  Pro
80                      85                      90                       95

Lys  Ile  Ala  Pro  Lys  Ser  Glu  Asn  Val  Val  Val  Thr  Val  Lys  Val  Met
                100                     105                     110

Gly  Asp  Asp  Gly  Val  Leu  Ala  Cys  Ala  Ile  Ala  Thr  His  Ala  Lys  Ile
               115                      120                     125

Arg  Asp
```

( 2 ) INFORMATION FOR SEQ ID NO:5:

( i ) SEQUENCE CHARACTERISTICS:
        ( A ) LENGTH: 1072 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 36..1001

( x i ) SEQUENCE DESCRIPTION: SEQ ID NO:5:

```
CGTTTTCTTC  CATCAAAATT  AAAAATTCAT  CAAAA  ATG  AAA  TTC  GTT  TTG  GCC         53
                                          Met  Lys  Phe  Val  Leu  Ala
                                          -98                 -95

ATT  GCC  TCT  TTG  TTG  GTA  TTG  AGC  ACT  GTT  TAT  GCT  CGT  CCA  GCT  TCA  101
Ile  Ala  Ser  Leu  Leu  Val  Leu  Ser  Thr  Val  Tyr  Ala  Arg  Pro  Ala  Ser
          -90                      -85                      -80

ATC  AAA  ACT  TTT  GAA  GAA  TTC  AAA  AAA  GCC  TTC  AAC  AAA  AAC  TAT  GCC  149
Ile  Lys  Thr  Phe  Glu  Glu  Phe  Lys  Lys  Ala  Phe  Asn  Lys  Asn  Tyr  Ala
     -75                      -70                      -65

ACC  GTT  GAA  GAG  GAA  GAA  GTT  GCC  CGT  AAA  AAC  TTT  TTG  GAA  TCA  TTG  197
Thr  Val  Glu  Glu  Glu  Glu  Val  Ala  Arg  Lys  Asn  Phe  Leu  Glu  Ser  Leu
```

| | | | | | | | | | | | | | | | | |
|---|---|---|---|---|---|---|---|---|---|---|---|---|---|---|---|---|
| −60 | | | | −55 | | | | −50 | | | | −45 | | | | |
| AAA | TAT | GTT | GAA | GCT | AAC | AAA | GGT | GCC | ATC | AAC | CAT | TTG | TCC | GAT | TTG | 245 |
| Lys | Tyr | Val | Glu | Ala | Asn | Lys | Gly | Ala | Ile | Asn | His | Leu | Ser | Asp | Leu | |
| | | | | −40 | | | | | −35 | | | | | −30 | | |
| TCA | TTG | GAT | GAA | TTC | AAA | AAC | CGT | TAT | TTG | ATG | AGT | GCT | GAA | GCT | TTT | 293 |
| Ser | Leu | Asp | Glu | Phe | Lys | Asn | Arg | Tyr | Leu | Met | Ser | Ala | Glu | Ala | Phe | |
| | | | −25 | | | | | −20 | | | | | −15 | | | |
| GAA | CAA | CTC | AAA | ACT | CAA | TTC | GAT | TTG | AAT | GCC | GAA | ACA | AGC | GCT | TGC | 341 |
| Glu | Gln | Leu | Lys | Thr | Gln | Phe | Asp | Leu | Asn | Ala | Glu | Thr | Ser | Ala | Cys | |
| | | −10 | | | | | −5 | | | | | −1 | 1 | | | |
| CGT | ATC | AAT | TCG | GTT | AAC | GTT | CCA | TCG | GAA | TTG | GAT | TTA | CGA | TCA | CTG | 389 |
| Arg | Ile | Asn | Ser | Val | Asn | Val | Pro | Ser | Glu | Leu | Asp | Leu | Arg | Ser | Leu | |
| | 5 | | | | | 10 | | | | | 15 | | | | 20 | |
| CGA | ACT | GTC | ACT | CCA | ATC | CGT | ATG | CAA | GGA | GGC | TGT | GGT | TCA | TGT | TGG | 437 |
| Arg | Thr | Val | Thr | Pro | Ile | Arg | Met | Gln | Gly | Gly | Cys | Gly | Ser | Cys | Trp | |
| | | | | 25 | | | | | 30 | | | | | 35 | | |
| GCT | TTC | TCT | GGT | GTT | GCC | GCA | ACT | GAA | TCA | GCT | TAT | TTG | GCC | TAC | CGT | 485 |
| Ala | Phe | Ser | Gly | Val | Ala | Ala | Thr | Glu | Ser | Ala | Tyr | Leu | Ala | Tyr | Arg | |
| | | | 40 | | | | | 45 | | | | | 50 | | | |
| AAC | ACG | TCT | TTG | GAT | CTT | TCT | GAA | CAG | GAA | CTC | GTC | GAT | TGC | GCA | TCT | 533 |
| Asn | Thr | Ser | Leu | Asp | Leu | Ser | Glu | Gln | Glu | Leu | Val | Asp | Cys | Ala | Ser | |
| | | 55 | | | | | 60 | | | | | 65 | | | | |
| CAA | CAC | GGA | TGT | CAC | GGC | GAT | ACA | ATA | CCA | AGA | GGC | ATC | GAA | TAC | ATC | 581 |
| Gln | His | Gly | Cys | His | Gly | Asp | Thr | Ile | Pro | Arg | Gly | Ile | Glu | Tyr | Ile | |
| | 70 | | | | | 75 | | | | | 80 | | | | | |
| CAA | CAA | AAT | GGT | GTC | GTT | GAA | GAA | AGA | AGC | TAT | CCA | TAC | GTT | GCA | CGA | 629 |
| Gln | Gln | Asn | Gly | Val | Val | Glu | Glu | Arg | Ser | Tyr | Pro | Tyr | Val | Ala | Arg | |
| 85 | | | | | 90 | | | | | 95 | | | | | 100 | |
| GAA | CAA | CGA | TGC | CGA | CGA | CCA | AAT | TCG | CAA | CAT | TAC | GGT | ATC | TCA | AAC | 677 |
| Glu | Gln | Arg | Cys | Arg | Arg | Pro | Asn | Ser | Gln | His | Tyr | Gly | Ile | Ser | Asn | |
| | | | | 105 | | | | | 110 | | | | | 115 | | |
| TAC | TGC | CAA | ATT | TAT | CCA | CCA | GAT | GTG | AAA | CAA | ATC | CGT | GAA | GCT | TTG | 725 |
| Tyr | Cys | Gln | Ile | Tyr | Pro | Pro | Asp | Val | Lys | Gln | Ile | Arg | Glu | Ala | Leu | |
| | | | 120 | | | | | 125 | | | | | 130 | | | |
| ACT | CAA | ACA | CAC | ACA | GCT | ATT | GCC | GTC | ATT | ATT | GGC | ATC | AAA | GAT | TTG | 773 |
| Thr | Gln | Thr | His | Thr | Ala | Ile | Ala | Val | Ile | Ile | Gly | Ile | Lys | Asp | Leu | |
| | | 135 | | | | | 140 | | | | | 145 | | | | |
| AGA | GCT | TTC | CAA | CAT | TAT | GAT | GGA | CGA | ACA | ATC | ATT | CAA | CAT | GAC | AAT | 821 |
| Arg | Ala | Phe | Gln | His | Tyr | Asp | Gly | Arg | Thr | Ile | Ile | Gln | His | Asp | Asn | |
| 150 | | | | | 155 | | | | | 160 | | | | | | |
| GGT | TAT | CAA | CCA | AAC | TAT | CAT | GCC | GTC | AAC | ATT | GTC | GGT | TAC | GGA | AGT | 869 |
| Gly | Tyr | Gln | Pro | Asn | Tyr | His | Ala | Val | Asn | Ile | Val | Gly | Tyr | Gly | Ser | |
| 165 | | | | | 170 | | | | | 175 | | | | | 180 | |
| ACA | CAA | GGC | GAC | GAT | TAT | TGG | ATC | GTA | CGA | AAC | AGT | TGG | GAT | ACT | ACC | 917 |
| Thr | Gln | Gly | Asp | Asp | Tyr | Trp | Ile | Val | Arg | Asn | Ser | Trp | Asp | Thr | Thr | |
| | | | | 185 | | | | | 190 | | | | | 195 | | |
| TGG | GGA | GAT | AGC | GGA | TAC | GGA | TAT | TTC | CAA | GCC | GGA | AAC | AAC | CTC | ATG | 965 |
| Trp | Gly | Asp | Ser | Gly | Tyr | Gly | Tyr | Phe | Gln | Ala | Gly | Asn | Asn | Leu | Met | |
| | | | 200 | | | | | 205 | | | | | 210 | | | |
| ATG | ATC | GAA | CAA | TAT | CCA | TAT | GTT | GTA | ATC | ATG | TGAACATTTG | AAATTGAATA | | | | 1018 |
| Met | Ile | Glu | Gln | Tyr | Pro | Tyr | Val | Val | Ile | Met | | | | | | |
| | | 215 | | | | | 220 | | | | | | | | | |
| TATTTATTTG | TTTTCAAAAT | AAAAACAACT | ACTCTTGCGA | GTATTTTTA | CTCG | | | | | | | | | | | 1072 |

( 2 ) INFORMATION FOR SEQ ID NO:6:

( i ) SEQUENCE CHARACTERISTICS:
        ( A ) LENGTH: 321 amino acids
        ( B ) TYPE: amino acid
        ( D ) TOPOLOGY: linear (  i i  ) MOLECULE TYPE: protein (  x i  ) SEQUENCE DESCRIPTION: SEQ ID NO:6:

| Met -98 | Lys | Phe -95 | Val | Leu | Ala | Ile | Ala -90 | Ser | Leu | Val | Leu -85 | Ser | Thr | Val |
| Tyr | Ala | Arg -80 | Pro | Ala | Ser | Ile | Lys -75 | Thr | Phe | Glu | Glu | Phe -70 | Lys | Lys | Ala |
| Phe | Asn -65 | Lys | Asn | Tyr | Ala | Thr -60 | Val | Glu | Glu | Glu | Glu -55 | Val | Ala | Arg | Lys |
| Asn -50 | Phe | Leu | Glu | Ser | Leu -45 | Lys | Tyr | Val | Glu | Ala -40 | Asn | Lys | Gly | Ala | Ile -35 |
| Asn | His | Leu | Ser | Asp -30 | Leu | Ser | Leu | Asp | Glu -25 | Phe | Lys | Asn | Arg | Tyr -20 | Leu |
| Met | Ser | Ala | Glu -15 | Ala | Phe | Glu | Gln | Leu -10 | Lys | Thr | Gln | Phe | Asp -5 | Leu | Asn |
| Ala | Glu | Thr -1 | Ser 1 | Ala | Cys | Arg 5 | Ile | Asn | Ser | Val | Asn 10 | Val | Pro | Ser | Glu |
| Leu 15 | Asp | Leu | Arg | Ser | Leu 20 | Arg | Thr | Val | Thr | Pro 25 | Ile | Arg | Met | Gln | Gly 30 |
| Gly | Cys | Gly | Ser | Cys 35 | Trp | Ala | Phe | Ser | Gly 40 | Val | Ala | Ala | Thr | Glu 45 | Ser |
| Ala | Tyr | Leu | Ala | Tyr 50 | Arg | Asn | Thr | Ser | Leu 55 | Asp | Leu | Ser | Glu | Gln 60 | Glu |
| Leu | Val | Asp | Cys 65 | Ala | Ser | Gln | His | Gly 70 | Cys | His | Gly | Asp | Thr 75 | Ile | Pro |
| Arg | Gly | Ile 80 | Glu | Tyr | Ile | Gln | Gln 85 | Asn | Gly | Val | Val | Glu 90 | Glu | Arg | Ser |
| Tyr 95 | Pro | Tyr | Val | Ala | Arg 100 | Glu | Gln | Arg | Cys | Arg 105 | Arg | Pro | Asn | Ser | Gln 110 |
| His | Tyr | Gly | Ile | Ser 115 | Asn | Tyr | Cys | Gln | Ile 120 | Tyr | Pro | Pro | Asp | Val 125 | Lys |
| Gln | Ile | Arg | Glu 130 | Ala | Leu | Thr | Gln | Thr 135 | His | Thr | Ala | Ile | Ala 140 | Val | Ile |
| Ile | Gly | Ile 145 | Lys | Asp | Leu | Arg | Ala 150 | Phe | Gln | His | Tyr | Asp 155 | Gly | Arg | Thr |
| Ile | Ile 160 | Gln | His | Asp | Asn | Gly 165 | Tyr | Gln | Pro | Asn | Tyr 170 | His | Ala | Val | Asn |
| Ile | Val 175 | Gly | Tyr | Gly | Ser 180 | Thr | Gln | Gly | Asp | Asp 185 | Tyr | Trp | Ile | Val | Arg 190 |
| Asn | Ser | Trp | Asp | Thr 195 | Thr | Trp | Gly | Asp | Ser 200 | Gly | Tyr | Gly | Tyr | Phe 205 | Gln |
| Ala | Gly | Asn | Asn 210 | Leu | Met | Met | Ile | Glu 215 | Gln | Tyr | Pro | Tyr | Val 220 | Val | Ile |
| Met |

( 2 ) INFORMATION FOR SEQ ID NO:7:

( i ) SEQUENCE CHARACTERISTICS:
        ( A ) LENGTH: 491 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..390

( x i ) SEQUENCE DESCRIPTION: SEQ ID NO:7:

| | | | | | | | | | | | | | | | | |
|---|---|---|---|---|---|---|---|---|---|---|---|---|---|---|---|---|
| GAT | CAA | GTC | GAT | GTT | AAA | GAT | TGT | GCC | AAC | AAT | GAA | ATC | AAA | AAA | GTA | 48 |
| Asp | Gln | Val | Asp | Val | Lys | Asp | Cys | Ala | Asn | Asn | Glu | Ile | Lys | Lys | Val | |
| 1 | | | | 5 | | | | | 10 | | | | | 15 | | |
| ATG | GTC | GAT | GGT | TGC | CAT | GGT | TCT | GAT | CCA | TGC | ATA | ATC | CAT | CGT | GGT | 96 |
| Met | Val | Asp | Gly | Cys | His | Gly | Ser | Asp | Pro | Cys | Ile | Ile | His | Arg | Gly | |
| | | | 20 | | | | | 25 | | | | | 30 | | | |
| AAA | CCA | TTC | ACT | TTG | GAA | GCC | TTA | TTC | GAT | GCC | AAC | CAA | AAC | ACT | AAA | 144 |
| Lys | Pro | Phe | Thr | Leu | Glu | Ala | Leu | Phe | Asp | Ala | Asn | Gln | Asn | Thr | Lys | |
| | | 35 | | | | | 40 | | | | | 45 | | | | |
| ACC | GCT | AAA | ACT | GAA | ATC | AAA | GCC | AGC | CTC | GAT | GGT | CTT | GAA | ATT | GAT | 192 |
| Thr | Ala | Lys | Thr | Glu | Ile | Lys | Ala | Ser | Leu | Asp | Gly | Leu | Glu | Ile | Asp | |
| | 50 | | | | | 55 | | | | | 60 | | | | | |
| GTT | CCC | GGT | ATT | GAT | ACC | AAT | GCT | TGC | CAT | TTT | ATG | AAA | TGT | CCA | TTG | 240 |
| Val | Pro | Gly | Ile | Asp | Thr | Asn | Ala | Cys | His | Phe | Met | Lys | Cys | Pro | Leu | |
| 65 | | | | | 70 | | | | | 75 | | | | | 80 | |
| GTT | AAA | GGT | CAA | CAA | TAT | GAT | GCC | AAA | TAT | ACA | TGG | AAT | GTG | CCC | AAA | 288 |
| Val | Lys | Gly | Gln | Gln | Tyr | Asp | Ala | Lys | Tyr | Thr | Trp | Asn | Val | Pro | Lys | |
| | | | | 85 | | | | | 90 | | | | | 95 | | |
| ATT | GCA | CCA | AAA | TCT | GAA | AAC | GTT | GTC | GTT | ACA | GTC | AAA | CTT | GTT | GGT | 336 |
| Ile | Ala | Pro | Lys | Ser | Glu | Asn | Val | Val | Val | Thr | Val | Lys | Leu | Val | Gly | |
| | | | 100 | | | | | 105 | | | | | 110 | | | |
| GAT | AAT | GGT | GTT | TTG | GCT | TGC | GCT | ATT | GCT | ACC | CAC | GCT | AAA | ATC | CGT | 384 |
| Asp | Asn | Gly | Val | Leu | Ala | Cys | Ala | Ile | Ala | Thr | His | Ala | Lys | Ile | Arg | |
| | | 115 | | | | | 120 | | | | | 125 | | | | |
| GAT | TAAAAAAAAA | AAATAAATAT | GAAATTTTC | ACCAACATCG | AACAAAATTC | | | | | | | | | | | 437 |
| Asp | | | | | | | | | | | | | | | | |
| 130 | | | | | | | | | | | | | | | | |

AATAACCAAA ATTTGAATCA AAAACGGAAT TCCAAGCTGA GCGCCGGTCG CTAC 491

( 2 ) INFORMATION FOR SEQ ID NO:8:

( i ) SEQUENCE CHARACTERISTICS:
        ( A ) LENGTH: 129 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| | | | | | | | | | | | | | | | |
|---|---|---|---|---|---|---|---|---|---|---|---|---|---|---|---|
| Asp | Gln | Val | Asp | Val | Lys | Asp | Cys | Ala | Asn | Asn | Glu | Ile | Lys | Lys | Val |
| 1 | | | | 5 | | | | | 10 | | | | | 15 | |
| Met | Val | Asp | Gly | Cys | His | Gly | Ser | Asp | Pro | Cys | Ile | Ile | His | Arg | Gly |
| | | | 20 | | | | | 25 | | | | | 30 | | |
| Lys | Pro | Phe | Thr | Leu | Glu | Ala | Leu | Phe | Asp | Ala | Asn | Gln | Asn | Thr | Lys |
| | | 35 | | | | | 40 | | | | | 45 | | | |
| Thr | Ala | Lys | Thr | Glu | Ile | Lys | Ala | Ser | Leu | Asp | Gly | Leu | Glu | Ile | Asp |
| | 50 | | | | | 55 | | | | | 60 | | | | |
| Val | Pro | Gly | Ile | Asp | Thr | Asn | Ala | Cys | His | Phe | Met | Lys | Cys | Pro | Leu |
| 65 | | | | | 70 | | | | | 75 | | | | | 80 |
| Val | Lys | Gly | Gln | Gln | Tyr | Asp | Ala | Lys | Tyr | Thr | Trp | Asn | Val | Pro | Lys |
| | | | | 85 | | | | | 90 | | | | | 95 | |
| Ile | Ala | Pro | Lys | Ser | Glu | Asn | Val | Val | Val | Thr | Val | Lys | Leu | Val | Gly |
| | | | 100 | | | | | 105 | | | | | 110 | | |
| Asp | Asn | Gly | Val | Leu | Ala | Cys | Ala | Ile | Ala | Thr | His | Ala | Lys | Ile | Arg |
| | | 115 | | | | | 120 | | | | | 125 | | | |

Asp ( 2 ) INFORMATION FOR SEQ ID NO:9:

( i ) SEQUENCE CHARACTERISTICS:
        ( A ) LENGTH: 1172 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..738

( x i ) SEQUENCE DESCRIPTION: SEQ ID NO:9:

```
GAATTCCTTT TTTTTCTTT CTCTCTCTAA AATCTAAAAT CCATCCAAC ATG AAA ATT         58
                                                      Met Lys Ile
                                                       -98

GTT TTG GCC ATC GCC TCA TTG TTG GCA TTG AGC GCT GTT TAT GCT CGT         106
Thr Leu Ala Ile Ala Ser Leu Leu Ala Leu Ser Ala Val Tyr Ala Arg
-95             -90                 -85                     -80

CCA TCA TCG ATC AAA ACT TTT GAA GAA TAC AAA AAA GCC TTC AAC AAA         154
Pro Ser Ser Ile Lys Thr Phe Glu Glu Tyr Lys Lys Ala Phe Asn Lys
                -75              -70                     -65

AGT TAT GCT ACC TTC GAA GAT CAA GAA GCT GCC CGT AAA AAC TTT TTG         202
Ser Tyr Ala Thr Phe Glu Asp Gln Glu Ala Ala Arg Lys Asn Phe Leu
            -60              -55                     -50

GAA TCA GTA AAA TAT GTT CAA TCA AAT GGA GGT GCC ATC AAC CAT TTG         250
Glu Ser Val Lys Tyr Val Gln Ser Asn Gly Gly Ala Ile Asn His Leu
        -45                 -40                     -35

TCC GAT TTG TCG TTG GAT GAA TTC AAA AAC CGA TTT TTG ATG AGT GCA         298
Ser Asp Leu Ser Leu Asp Glu Phe Lys Asn Arg Phe Leu Met Ser Ala
    -30             -25                 -20

GAA GCT TTT GAA CAC CTC AAA ACT CAA TTC GAT TTG AAT GCT GAA ACT         346
Glu Ala Phe Glu His Leu Lys Thr Gln Phe Asp Leu Asn Ala Glu Thr
-15             -10                  -5                  -1   1

AAC GCC TGC AGT ATC AAT GGA AAT GCT CCA GCT GAA ATC GAT TTG CGA         394
Asn Ala Cys Ser Ile Asn Gly Asn Ala Pro Ala Glu Ile Asp Leu Arg
                 5               10                  15

CAA ATG CGA ACT GTC ACT CCC ATT CGT ATG CAA GGA GGC TGT GGT TCA         442
Gln Met Arg Thr Val Thr Pro Ile Arg Met Gln Gly Gly Cys Gly Ser
         20              25                  30

TGT TGG GCT TTC TCT GGT GTT GCC GCA ACT GAA TCA GCT TAT TTG GCT         490
Cys Trp Ala Phe Ser Gly Val Ala Ala Thr Glu Ser Ala Tyr Leu Ala
     35              40                  45

CAC CGT AAT CAA TCA TTG GAT CTT GCT GAA CAA GAA TTA GTC GAT TGT         538
His Arg Asn Gln Ser Leu Asp Leu Ala Glu Gln Glu Leu Val Asp Cys
 50              55                  60                      65

GCT TCC CAA CAC GGT TGT CAT GGT GAT ACC ATT CCA CGT GGT ATT GAA         586
Ala Ser Gln His Gly Cys His Gly Asp Thr Ile Pro Arg Gly Ile Glu
                  70                  75                      80

TAC ATC CAA CAT AAT GGT GTC GTC CAA GAA AGC TAC TAT CGA TAC GTT         634
Tyr Ile Gln His Asn Gly Val Val Gln Glu Ser Tyr Tyr Arg Tyr Val
              85                  90                      95

GCA CGA GAA CAA TCA TGC CGA CGA CCA AAT GCA CAA CGT TTC GGT ATC         682
Ala Arg Glu Gln Ser Cys Arg Arg Pro Asn Ala Gln Arg Phe Gly Ile
         100             105                 110

TCA AAC TAT TGC CAA ATT TAC CCA CCA AAT GCA AAC AAA ATT CGT GAA         730
Ser Asn Tyr Cys Gln Ile Tyr Pro Pro Asn Ala Asn Lys Ile Arg Glu
         115             120                 125

GCT TTG GCT CAA ACC CAC AGC GCT ATT GCC GTC ATT ATT GGC ATC AAA         778
Ala Leu Ala Gln Thr His Ser Ala Ile Ala Val Ile Ile Gly Ile Lys
130              135                 140                     145
```

```
GAT  TTA  GAC  GCA  TTC  CGT  CAT  TAT  GAT  GGC  CGA  ACA  ATC  ATT  CAA  CGC    826
Asp  Leu  Asp  Ala  Phe  Arg  His  Tyr  Asp  Gly  Arg  Thr  Ile  Ile  Gln  Arg
               150                     155                         160

GAT  AAT  GGT  TAC  CAA  CCA  AAC  TAT  CAC  GCT  GTC  AAC  ATT  GTT  GGT  TAC    874
Asp  Asn  Gly  Tyr  Gln  Pro  Asn  Tyr  His  Ala  Val  Asn  Ile  Val  Gly  Tyr
               165                     170                    175

AGT  AAC  GCA  CAA  GGT  GTC  GAT  TAT  TGG  ATC  GTA  CGA  AAC  AGT  TGG  GAT    922
Ser  Asn  Ala  Gln  Gly  Val  Asp  Tyr  Trp  Ile  Val  Arg  Asn  Ser  Trp  Asp
          180                          185                    190

ACC  AAT  TGG  GGT  GAT  AAT  GGT  TAC  GGT  TAT  TTT  GCT  GCC  AAC  ATC  GAT    970
Thr  Asn  Trp  Gly  Asp  Asn  Gly  Tyr  Gly  Tyr  Phe  Ala  Ala  Asn  Ile  Asp
     195                         200                    205

TTG  ATG  ATG  ATT  GAA  GAA  TAT  CCA  TAT  GTT  GTC  ATT  CTC  TAAACAAAAA      1019
Leu  Met  Met  Ile  Glu  Glu  Tyr  Pro  Tyr  Val  Val  Ile  Leu
210                      215                    220

GACAATTTCT  TATATGATTG  TCACTAATTT  ATTTAAAATC  AAAATTTTTA  GAAAATGAAT             1079

AAATTCATTC  ACAAAAATTA  AAAAAAAAAA  AAAAAAAAAA  AAAAAAAAAA  AAAAAAAAAA             1139

AAAAAAAAAA  AAAAAAAAAA  AAAAAAAAAA  AAA                                            1172
```

( 2 ) INFORMATION FOR SEQ ID NO:10:

( i ) SEQUENCE CHARACTERISTICS:
        ( A ) LENGTH: 320 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Met  Lys  Ile  Thr  Leu  Ala  Ile  Ala  Ser  Leu  Leu  Ala  Leu  Ser  Ala  Val
-98            -95                 -90                      -85

Tyr  Ala  Arg  Pro  Ser  Ser  Ile  Lys  Thr  Phe  Glu  Glu  Tyr  Lys  Lys  Ala
          -80                      -75                      -70

Phe  Asn  Lys  Ser  Tyr  Ala  Thr  Phe  Glu  Asp  Glu  Glu  Ala  Ala  Arg  Lys
     -65                      -60                      -55

Asn  Phe  Leu  Glu  Ser  Val  Lys  Tyr  Val  Gln  Ser  Asn  Gly  Gly  Ala  Ile
-50                      -45                      -40                      -35

Asn  His  Leu  Ser  Asp  Leu  Ser  Leu  Asp  Glu  Phe  Lys  Asn  Arg  Phe  Leu
               -30                      -25                          -20

Met  Ser  Ala  Glu  Ala  Phe  Glu  His  Leu  Lys  Thr  Gln  Phe  Asp  Leu  Asn
               -15                      -10                         -5

Ala  Glu  Thr  Asn  Ala  Cys  Ser  Ile  Asn  Gly  Asn  Ala  Pro  Ala  Glu  Ile
          -1   1                    5                         10

Asp  Leu  Arg  Gln  Met  Arg  Thr  Val  Thr  Pro  Ile  Arg  Met  Gln  Gly  Gly
15                       20                      25                         30

Cys  Gly  Ser  Cys  Trp  Ala  Phe  Ser  Gly  Val  Ala  Ala  Thr  Glu  Ser  Ala
               35                       40                      45

Tyr  Leu  Ala  His  Arg  Asn  Gln  Ser  Leu  Asp  Leu  Ala  Glu  Gln  Glu  Leu
               50                       55                      60

Val  Asp  Cys  Ala  Ser  Gln  His  Gly  Cys  His  Gly  Asp  Thr  Ile  Pro  Arg
          65                       70                      75

Gly  Ile  Glu  Tyr  Ile  Gln  His  Asn  Gly  Val  Val  Gln  Glu  Ser  Tyr  Tyr
     80                       85                      90

Arg  Tyr  Val  Ala  Arg  Glu  Gln  Ser  Cys  Arg  Arg  Pro  Asn  Ala  Gln  Arg
95                       100                     105                        110

Phe  Gly  Ile  Ser  Asn  Tyr  Cys  Gln  Ile  Tyr  Pro  Pro  Asn  Ala  Asn  Lys
                    115                     120                        125
```

```
Ile  Arg  Glu  Ala  Leu  Ala  Gln  Thr  His  Ser  Ala  Ile  Ala  Val  Ile  Ile
               130                      135                      140

Gly  Ile  Lys  Asp  Leu  Asp  Ala  Phe  Arg  His  Tyr  Asp  Gly  Arg  Thr  Ile
               145                      150                      155

Ile  Gln  Arg  Asp  Asn  Gly  Tyr  Gln  Pro  Asn  Tyr  His  Ala  Val  Asn  Ile
     160                      165                      170

Val  Gly  Tyr  Ser  Asn  Ala  Gln  Gly  Val  Asp  Tyr  Trp  Ile  Val  Arg  Asn
175                           180                      185                      190

Ser  Trp  Asp  Thr  Asn  Trp  Gly  Asp  Asn  Gly  Tyr  Gly  Tyr  Phe  Ala  Ala
                    195                      200                      205

Asn  Ile  Asp  Leu  Met  Met  Ile  Glu  Glu  Tyr  Pro  Tyr  Val  Val  Ile  Leu
               210                      215                      220
```

( 2 ) INFORMATION FOR SEQ ID NO:11:

( i ) SEQUENCE CHARACTERISTICS:
( A ) LENGTH: 222 amino acids
( B ) TYPE: amino acid
( D ) TOPOLOGY: linear ( i i ) MOLECULE TYPE: protein ( i x ) FEATURE:
( A ) NAME/KEY: misc feature
( B ) LOCATION: 50
( D ) OTHER INFORMATION: /label=Xaa is His or Tyr ( i x ) FEATURE:
( A ) NAME/KEY: misc feature
( B ) LOCATION: 81
( D ) OTHER INFORMATION: /label=Xaa is Glu or Lys ( i x ) FEATURE:
( A ) NAME/KEY: misc feature
( B ) LOCATION: 124
( D ) OTHER INFORMATION: /label=Xaa is Ala or Val ( i x ) FEATURE:
( A ) NAME/KEY: misc feature
( B ) LOCATION: 136
( D ) OTHER INFORMATION: /label=Xaa is Ser or Thr ( i x ) FEATURE:
( A ) NAME/KEY: misc feature
( B ) LOCATION: 215
( D ) OTHER INFORMATION: /label=Xaa is Glu or Gln ( x i ) SEQUENCE DESCRIPTION: SEQ ID NO:11:

```
Thr  Asn  Ala  Cys  Ser  Ile  Asn  Gly  Asn  Ala  Pro  Ala  Glu  Ile  Asp  Leu
1                   5                        10                           15

Arg  Gln  Met  Arg  Thr  Val  Thr  Pro  Ile  Arg  Met  Gln  Gly  Gly  Cys  Gly
               20                       25                      30

Ser  Cys  Trp  Ala  Phe  Ser  Gly  Val  Ala  Ala  Thr  Glu  Ser  Ala  Tyr  Leu
               35                       40                      45

Ala  Xaa  Arg  Asn  Gln  Ser  Leu  Asp  Leu  Ala  Glu  Gln  Glu  Leu  Val  Asp
          50                       55                      60

Cys  Ala  Ser  Gln  His  Gly  Cys  His  Gly  Asp  Thr  Ile  Pro  Arg  Gly  Ile
65                       70                      75                           80

Xaa  Tyr  Ile  Gln  His  Asn  Gly  Val  Val  Gln  Glu  Ser  Tyr  Tyr  Arg  Tyr
               85                       90                           95

Val  Ala  Arg  Glu  Gln  Ser  Cys  Arg  Arg  Pro  Asn  Ala  Gln  Arg  Phe  Gly
               100                      105                     110

Ile  Ser  Asn  Tyr  Cys  Gln  Ile  Tyr  Pro  Pro  Asn  Xaa  Asn  Lys  Ile  Arg
               115                      120                     125
```

| Glu | Ala | Leu | Ala | Gln | Thr | His | Xaa | Ala | Ile | Ala | Val | Ile | Ile | Gly | Ile |
| --- | --- | --- | --- | --- | --- | --- | --- | --- | --- | --- | --- | --- | --- | --- | --- |
| 130 | | | | | | 135 | | | | | 140 | | | | |
| Lys | Asp | Leu | Asp | Ala | Phe | Arg | His | Tyr | Asp | Gly | Arg | Thr | Ile | Ile | Gln |
| 145 | | | | | 150 | | | | | 155 | | | | | 160 |
| Arg | Asp | Asn | Gly | Tyr | Gln | Pro | Asn | Tyr | His | Ala | Val | Asn | Ile | Val | Gly |
| | | | 165 | | | | | | 170 | | | | | 175 | |
| Tyr | Ser | Asn | Ala | Gln | Gly | Val | Asp | Tyr | Trp | Ile | Val | Arg | Asn | Ser | Trp |
| | | | 180 | | | | | 185 | | | | | 190 | | |
| Asp | Thr | Asn | Trp | Gly | Asp | Asn | Gly | Tyr | Gly | Tyr | Phe | Ala | Ala | Asn | Ile |
| | | 195 | | | | | 200 | | | | | 205 | | | |
| Asp | Leu | Met | Met | Ile | Glu | Xaa | Tyr | Pro | Tyr | Val | Val | Ile | Leu | | |
| | 210 | | | | | 215 | | | | | 220 | | | | |

( 2 ) INFORMATION FOR SEQ ID NO:12:

( i ) SEQUENCE CHARACTERISTICS:
        ( A ) LENGTH: 129 amino acids
        ( B ) TYPE: amino acid
        ( D ) TOPOLOGY: linear ( i i ) MOLECULE TYPE: protein ( i x ) FEATURE:
        ( A ) NAME/KEY: misc feature
        ( B ) LOCATION: 47
        ( D ) OTHER INFORMATION: /label=Xaa is Thr or Ser ( i x ) FEATURE:
        ( A ) NAME/KEY: misc feature
        ( B ) LOCATION: 114
        ( D ) OTHER INFORMATION: /label=Xaa is Asp or Asn ( i x ) FEATURE:
        ( A ) NAME/KEY: misc feature
        ( B ) LOCATION: 127
        ( D ) OTHER INFORMATION: /label=Xaa is Ile or Leu ( x i ) SEQUENCE DESCRIPTION: SEQ ID NO:12:

| Asp | Gln | Val | Asp | Val | Lys | Asp | Cys | Ala | Asn | His | Glu | Ile | Lys | Lys | Val |
| --- | --- | --- | --- | --- | --- | --- | --- | --- | --- | --- | --- | --- | --- | --- | --- |
| 1 | | | | 5 | | | | | 10 | | | | | 15 | |
| Leu | Val | Pro | Gly | Cys | His | Gly | Ser | Glu | Pro | Cys | Ile | Ile | His | Arg | Gly |
| | | | 20 | | | | | 25 | | | | | 30 | | |
| Lys | Pro | Phe | Gln | Leu | Glu | Ala | Val | Phe | Glu | Ala | Asn | Gln | Asn | Xaa | Lys |
| | | | 35 | | | | | 40 | | | | | 45 | | |
| Thr | Ala | Lys | Ile | Glu | Ile | Lys | Ala | Ser | Ile | Asp | Gly | Leu | Glu | Val | Asp |
| | | 50 | | | | | 55 | | | | | 60 | | | |
| Val | Pro | Gly | Ile | Asp | Pro | Asn | Ala | Cys | His | Tyr | Met | Lys | Cys | Pro | Leu |
| 65 | | | | | 70 | | | | | 75 | | | | | 80 |
| Val | Lys | Gly | Gln | Gln | Tyr | Asp | Ile | Lys | Tyr | Thr | Trp | Asn | Val | Pro | Lys |
| | | | | 85 | | | | | 90 | | | | | 95 | |
| Ile | Ala | Pro | Lys | Ser | Glu | Asn | Val | Val | Val | Thr | Val | Lys | Val | Met | Gly |
| | | | 100 | | | | | 105 | | | | | 110 | | |
| Asp | Xaa | Gly | Val | Leu | Ala | Cys | Ala | Ile | Ala | Thr | His | Ala | Lys | Xaa | Arg |
| | | 115 | | | | | 120 | | | | | 125 | | | |
| Asp | | | | | | | | | | | | | | | |

( 2 ) INFORMATION FOR SEQ ID NO:13:

( i ) SEQUENCE CHARACTERISTICS:
        ( A ) LENGTH: 129 amino acids
        ( B ) TYPE: amino acid
        ( D ) TOPOLOGY: linear ( i i ) MOLECULE TYPE: protein (ix) FEATURE:
  (A) NAME/KEY: misc feature
  (B) LOCATION: 11
  (D) OTHER INFORMATION: /label=Xaa is Asn or Ser (ix) FEATURE:
  (A) NAME/KEY: misc feature
  (B) LOCATION: 52
  (D) OTHER INFORMATION: /label=Xaa is Thr or Ile (ix) FEATURE:
  (A) NAME/KEY: misc feature
  (B) LOCATION: 54
  (D) OTHER INFORMATION: /label=Xaa is Ile or Thr (ix) FEATURE:
  (A) NAME/KEY: misc feature
  (B) LOCATION: 76
  (D) OTHER INFORMATION: /label=Xaa is Met or Val (ix) FEATURE:
  (A) NAME/KEY: misc feature
  (B) LOCATION: 88
  (D) OTHER INFORMATION: /label=Xaa is Ala or Ile (ix) FEATURE:
  (A) NAME/KEY: misc feature
  (B) LOCATION: 111
  (D) OTHER INFORMATION: /label=Xaa is Val or Ile (xi) SEQUENCE DESCRIPTION: SEQ ID NO:13:

Asp Gln Val Asp Val Lys Asp Cys Ala Asn Xaa Glu Ile Lys Lys Val
 1               5                        10                      15
Met Val Asp Gly Cys His Gly Ser Asp Pro Cys Ile Ile His Arg Gly
              20                      25                      30
Lys Pro Phe Thr Leu Glu Ala Leu Phe Asp Ala Asn Gln Asn Thr Lys
          35                      40                      45
Thr Ala Lys Xaa Glu Xaa Lys Ala Ser Leu Asp Gly Leu Glu Ile Asp
      50                      55                  60
Val Pro Gly Ile Asp Thr Asn Ala Cys His Phe Xaa Lys Cys Pro Leu
 65                  70                      75                      80
Val Lys Gly Gln Gln Tyr Asp Xaa Lys Tyr Thr Trp Asn Val Pro Lys
              85                      90                      95
Ile Ala Pro Lys Ser Glu Asn Val Val Val Thr Val Lys Leu Xaa Gly
              100                     105                     110
Asp Asn Gly Val Leu Ala Cys Ala Ile Ala Thr His Ala Lys Ile Arg
              115                     120                     125
Asp

CLONING AND SEQUENCING OF ALLERGENS OF DERMATOPHAGOIDES (HOUSE DUST MITE)

This application is a divisional application of Ser. No. 07/945,288 filed on Sep. 10, 1992, now U.S. Pat. No. 5,433,948, which in turn is a continuation-in-part application of Ser. No. 580,655 filed on Sep. 11, 1990, now abandoned which in turn is a continuation-in-part application of Ser. No. 458,642 filed on Feb. 13, 1990, now abandoned. This application also claims priority to an international application, PCT/AU91/00417 filed on Sep. 10, 1991. The contents of all of the aforementioned application (s) are hereby incorporated by reference.

RELATED APPLICATIONS

This application is a continuation-in-part of U.S. Ser. No. 580,655, entitled "Cloning and Sequencing of Allergens of Dermatophagoides (House Dust Mite)", filed Sep. 11, 1990, which is a continuation-in-part of U.S. Ser. No. 458,642, entitled "Cloning of Mite Allergens," filed Feb. 13, 1990. This application also claims priority to an international application, PCT/AU91/00417, filed Sep. 10, 1991. The contents of these applications are incorporated herein by reference.

BACKGROUND

Recent reports have documented the importance of responses to the Group I and Group II allergens in house dust mite allergy. For example, it has been documented that over 60% of patients have at least 50% of their anti-mite antibodies directed towards these proteins (Lind, P. et al., *Allergy*, 39:259–274 (1984); van der Zee, J. S. et al., *J. Allergy Clin. Immunol.*, 8:884–896 (1988)). It is possible that children show a greater degree of reactivity (Thompson, P. J. et al., *Immunology* 64:311–314 (1988)). Allergy to mites of the genus Dermatophagoides (D.) is associated with conditions such as asthma, rhinitis and ectopic dermatitis. Two species, *D. pteronyssinus* and *D. farinae*, predominate and, as a result, considerable effort has been expended in trying to identify the allergens produced by these two species. *D. pteronyssinus* mites are the most common Dermatophagoides species in house dust in Western Europe and Australia. The species *D. farinae* predominates in other countries, such as North America and Japan (Wharton, G. W., *J. Medical Entom*, 12:577–621 (1976)). It has long been recognized that allergy to mites of this genus is associated with diseases such as asthma, rhinitis and atopic dermatitis. It is still not clear what allergens produced by these mites are responsible for the allergic response and associated conditions.

SUMMARY OF THE INVENTION

The present invention relates to isolated DNA which encodes a protein allergen of Dermatophagoides ((D.) house dust mite) or a peptide which includes at least one epitope of a protein allergen of a house dust mite of the genus Dermatophagoides. It particularly relates to DNA encoding major allergens of the species *D. farinae*, designated Der f I and Der f II, or portions of these major allergens (i.e., peptides which include at least one epitope of Der f I or of Der f II). It also particularly relates to DNA encoding major allergens of *D. pteronyssinus*, designated Der p I and Der p II, or portions of these major allergens (i.e., peptides which include at least one epitope of Der p I or of Der p II).

The present invention further relates to proteins and peptides encoded by the isolated Dermatophagoides (e.g., *D. farinae, D. pteronyssinus*) DNA including proteins containing sequence polymorphisms. Several nucleotide and resulting amino acid sequence polymorphisms have been discovered in the Der p I, Der p II and Der f II allergens. All such nucleotide variations and proteins, or portions thereof, containing a sequence polymorphism are within the scope of the invention.

Peptides of the present invention include at least one epitope of a *D. farinae* allergen (e.g., at least one epitope of Der f I or Der f II) or at least one epitope of a *D. pteronyssinus* allergen (e.g., at least one epitope of Der p I or of Der p II). It also relates to antibodies specific for *D. farinae* proteins or peptides and to antibodies specific for *D. pteronyssinus* proteins or peptides.

Dermatophagoides DNA, proteins and peptides of the present invention are useful for diagnostic and therapeutic purposes. For example, isolated *D. farinae* proteins or peptides can be used to detect sensitivity in an individual to house dust mites and can be used to treat sensitivity (reduce sensitivity or desensitize) in an individual, to whom therapeutically effective quantities of the *D. farinae* protein or peptide is administered. For example, isolated *D. farinae* protein allergen, such as Der f I or Der f II, can be administered periodically, using standard techniques, to an individual in order to desensitize the individual. Alternatively, a peptide which includes at least one epitope of Der f I or of Der f II can be administered for this purpose. Isolated *D. pteronyssinus* protein allergen, such as Der p I or Der p II, can be administered as described for Der f I or Der f II. Similarly, a peptide which includes at least one Der p I epitope or at least one Der p II epitope can be administered for this purpose. A combination of these proteins or peptides (e.g., Der f I and Der f II; Der p and Der p II; or a mixture of both Der f and Der p proteins) can also be administered. The use of such isolated proteins or peptides provides a means of desensitizing individuals to important house dust mite allergens.

BRIEF DESCRIPTION OF THE DRAWINGS

FIG. 1A and 1B show the nucleotide and predicted amino acid sequence of cDNA λgt11 p1(13T). Numbers to the right are nucleotide positions whereas numbers above the sequence are amino acid positions. Positive amino acid residue numbers correspond to the sequence of the mature excreted Der p I beginning with threonine. Negative sequence numbers refer to the proposed transient pre- and preproenzyme forms of Der p I. The arrows indicate the beginning of the proposed proenzyme sequence and the mature Der p I, respectively. Residues −15 to −13 enclosed by an open box make up the proposed cleavage for the proenzyme formation, and the dashed residues 52-54 represent a potential N-glycosylation site. The termination TAA codon and the adjacent polyadenylation signal are underlined. Amino acid residues 1-41, 79-95, 111-142, and 162-179 correspond to known tryptic peptide sequences determined by conventional amino acid sequencing analysis.

FIG. 3 is a comparison of N-terminal sequences of Der p I and Der f I. The amino acid sequence for Der p I is equivalent to amino acids 1-20 in FIG. 1; the Der f I sequence is from reference (12).

FIG. 4 shows the reactivity of λgt11 p1(13T) with anti-Der p I. Lysates from Y1089 lysogens induced for phage were reacted by dot-blot with rabbit anti-Der p I (Der p I)

or normal rabbit serum (Nrs). Dots (2 μl) were made in triplicate from lysates of bacteria infected with λgt11 p1(13T) (a) or λgt11 (b). When developed with $^{125}$I-protein A and autoradiography only the reaction between λgt11 p1(13T) lysate and the anti-*Der p* I showed reactivity.

Figure 5:
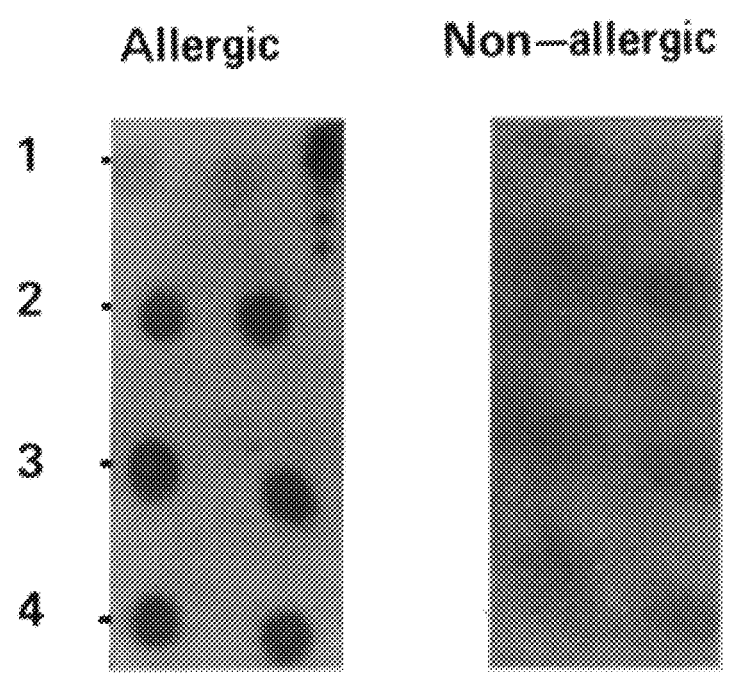

FIG. 5 shows reaction of clone pGEX-p1(13T) with IgE in allergic serum. Overnight cultures of pGEX or pGEX-p1 where diluted 1/10 in broth and grown for 2 hours at 37° C. They were induced with IPTG, grown for 2 hours at 37° C. The bacteria were pelletted and resuspended in PBS to 1/10 the volume of culture media. The bacteria were lysed by freeze/thaw and sonication. A radioimmune dot-blot was performed with 2 μl of these lysates using mite-allergic or non-allergic serum. The dots in row 1 were from *E. coli* containing pGEX and row 2–4 from different cultures of *E. coli* infected with pGEX-p1(13T). Reactivity to pGEX-p1 (13T) was found with IgE in allergic but not non-allergic serum. No reactivity to the vector control or with non-allergic serum was found.

Figure 6:
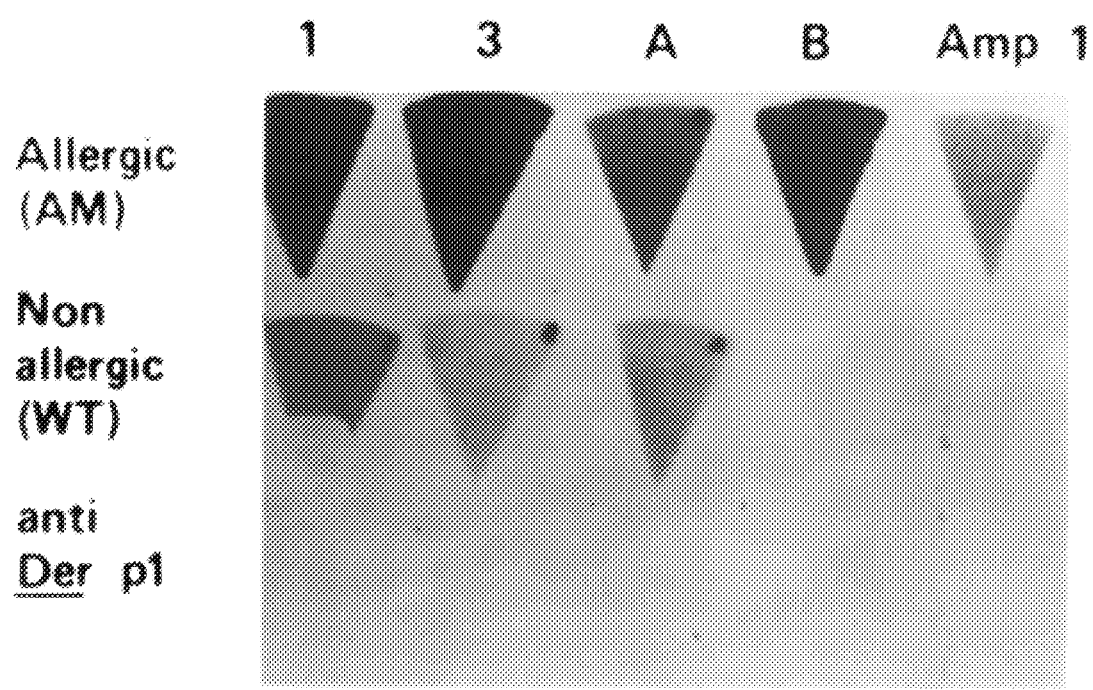

FIG. 6 shows seroreactivity of cDNA clones coding for *Der p* II in plaque radioimmune assay. Segments of nitrocellulose filters from plaque lifts were taken from clones 1, 3, A, B and the vector control Amp1. These were reached by immunoassay for human IgE against allergic serum (AM) in row 1, non-allergic serum (WT) in row 2 and by protein A immunoassay for *Der p* I with rabbit antiserum in row 3. The clones 1, 3 and B reacted strongly with allergic serum but not non-allergic or vector control. (Clone B and vector control were not tested with non-allergic serum).

FIGS. 7A and 7B shows the nucleotide and predicted amino acid sequence of cDNA of λgt11 p II (C1). Numbers to the right are nucleotide positions and numbers above are amino acid positions. Positive numbers for amino acids begin at the known N-terminal of *Der p* II and match the known sequence of the first 40 residues. Residues -1 to -16 resemble a typical leader sequence with a hydrophobic core.

FIG. 8 shows the N-terminal amino acid homology of *Der p* II and *Der f* II. (*Der f* II sequence from reference 30).

Figure 9:
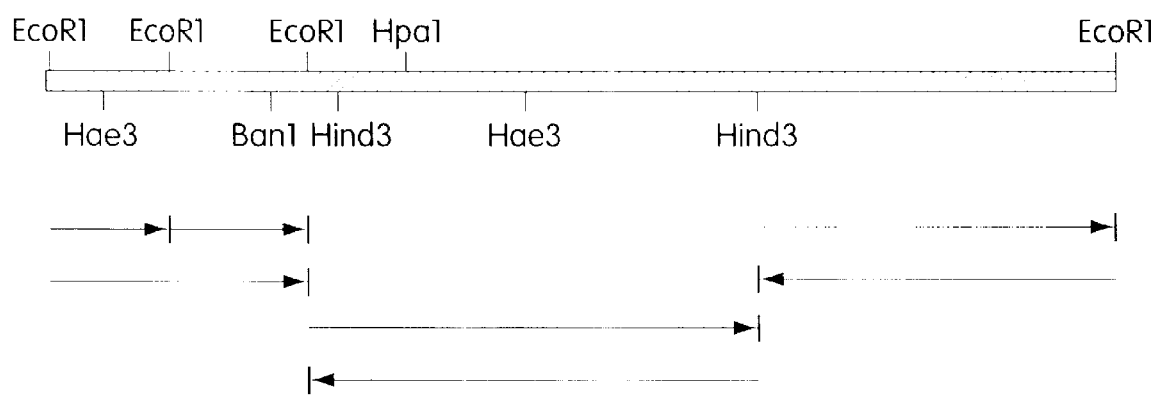

FIG. 9 is a restriction map of the cDNA insert of clone λgt11 f 1, including a schematic representation of the strategy of DNA sequencing. Arrows indicate directions in which sequences were read.

FIGS. 10A and 10B is the nucleotide sequence and the predicted amino acid sequence of cDNA λgt11 f 1. Numbers above are nucleotide positions; numbers to the left are amino acid positions. Positive amino acid residue numbers correspond to the sequence of the mature excreted *Der f* I beginning with threonine. Negative sequence numbers refer to the signal peptide and the proenzyme regions of *Der f* I. The arrows indicate the beginning of the proenzyme sequence and the mature *Der f* I, respectively. The underlined residues -81 to -78 make up the proposed cleavage site for the proenzyme formation, while the underlined residues 53-55 represent a potential N-glycosylation site. The termination TGA codon and the adjacent polyadenylation signal are also underlined. Amino acid residues 1-28 correspond to a known tryptic peptide sequence determined by conventional amino acid sequencing analysis.

FIG. 11 is a composite alignment of the amino acid sequences of the mature *Der p* I and *Der f* I proteins. The numbering above the sequence refers to *Der p* I. The asterisk denotes the gap that was introduced for maximal alignment. The symbol (.) is used to indicate that the amino acid residue of *Der f* I at that position is identical to the corresponding amino acid residue of *Der p* I. The arrows indicate those residues making up the active site of *Der p* I and *Der f* I.

FIGS. 12A and 12B is a comparison of the amino acid sequence in the pre- and pro-peptide regions of *Der f* I with those of rat cathepsin H, rat cathepsin L, papain, aleurain, CP1, CP2, rat cathepsin B, CTLA-2, MCP, *Der p* I and actinidin. Gaps, denoted by dashes, were added for maximal alignment. Double asterisks denote conserved amino acid residues which are shared by greater than 80% of the proenzymes; single asterisks show residues which are conserved in greater than 55% of the sequences. The symbol (.) is used to denote semiconserved equivalent amino acids which are shared by greater than 90% of the proenzyme regions.

Figure 13A:
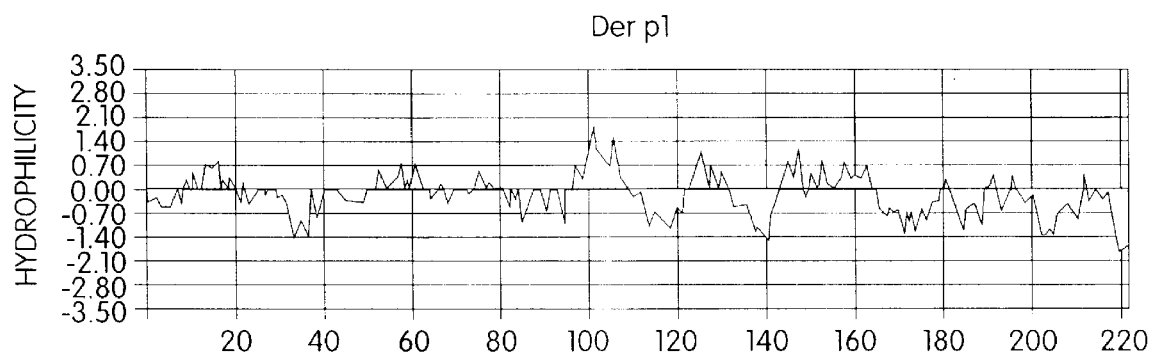
Figure 13B:
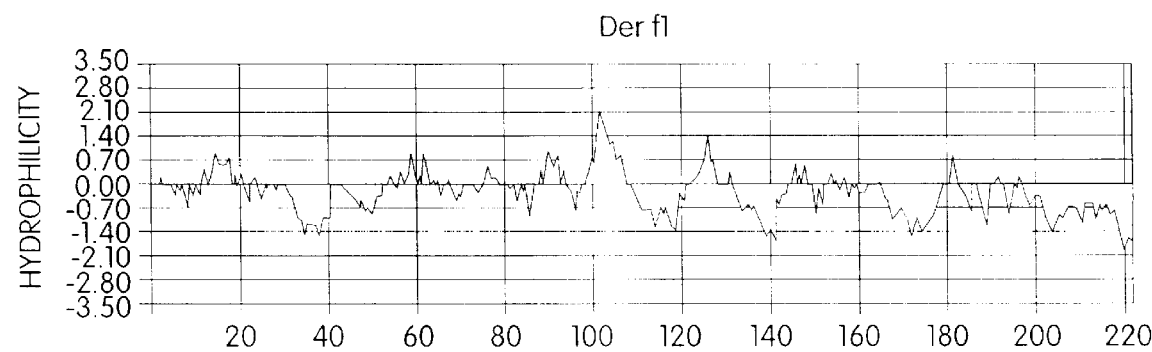

FIGS. 13A and 13B is a hydrophilicity plot of the *Der p* I mature protein and a hydrophilicity plot of the *Der f* I mature protein produced using the Hopp-Woods algorithm computed with the Mac Vector Sequence Analysis Software (IBI, New Haven) using a 6 residue window. Positive values indicate relative hydrophilicity and negative values indicating relative hydrophobicity.

FIG. 14 is the nucleotide sequence and the predicted amino acid sequence of *Der f* II cDNA. Numbers to the right are nucleotide positions and numbers above are amino acid residues. The stop (TAA) signal is underlined. The first 8 nucleotides are from the oligonucleotide primer used to generate the cDNA, based on the *Der p* II sequence.

Figure 15:
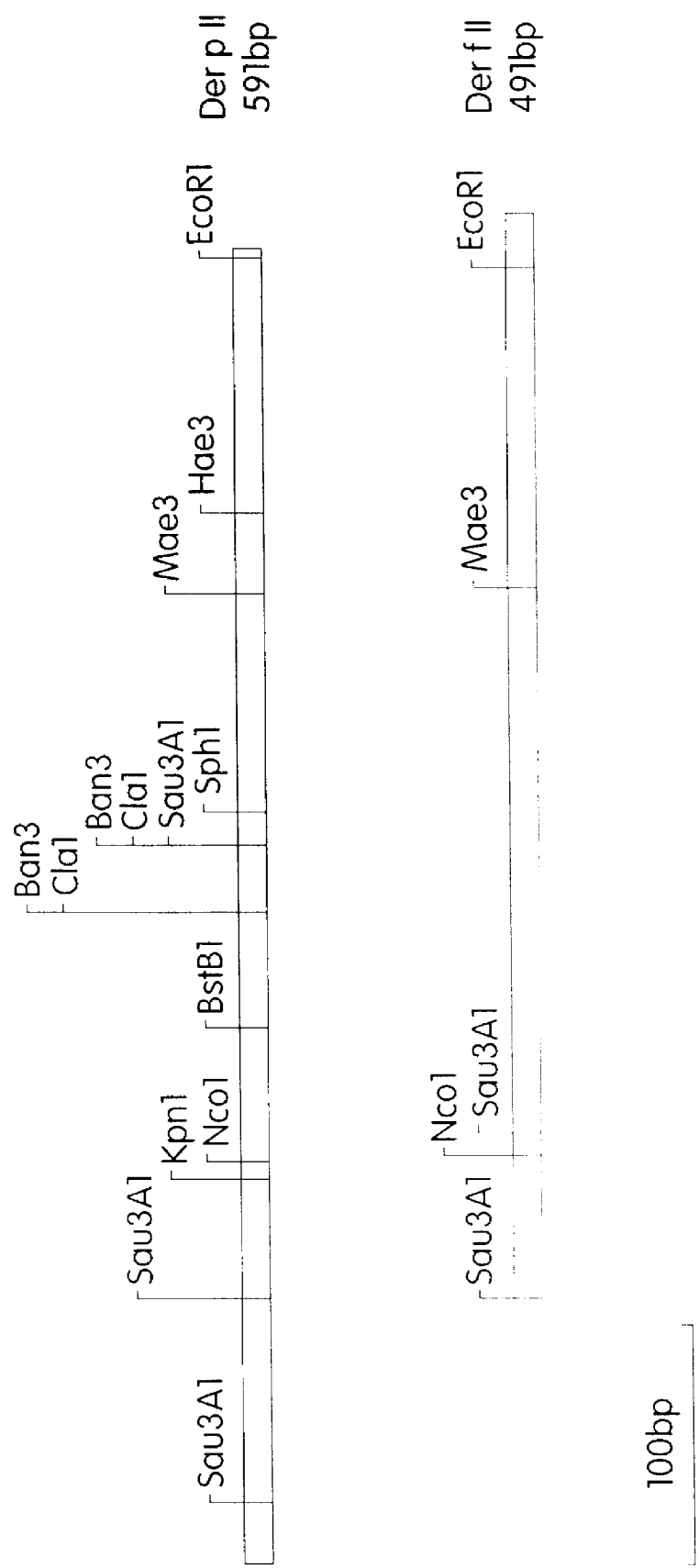

FIG. 15 is a restriction map of *Der f* II cDNA, which was generated by computer from the sequence data. A map of *Der p* II similarly generated is shown for comparison. There are few common restriction enzyme sites conserved. Sites marked with an asterisk were introduced by cloning procedures.

FIGS. 16A, 16B and 16C shows the alignment of *Der f* II and *Der p* II cDNA sequences. Numbers to the right are nucleotide position and numbers above are amino acid residues. The top line gives *Der p* II nucleotide sequence and the second the *Der p* II amino acid residues. The next two lines show differences of *Der f* II to these sequences.

Figure 17A:
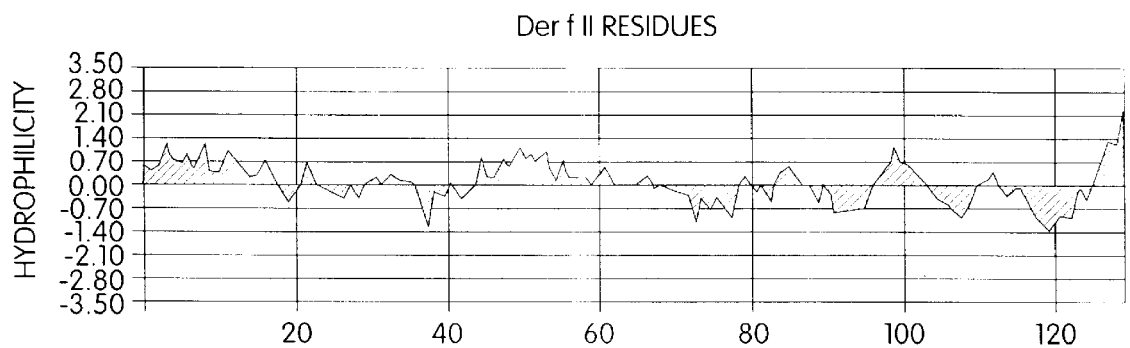
Figure 17B:
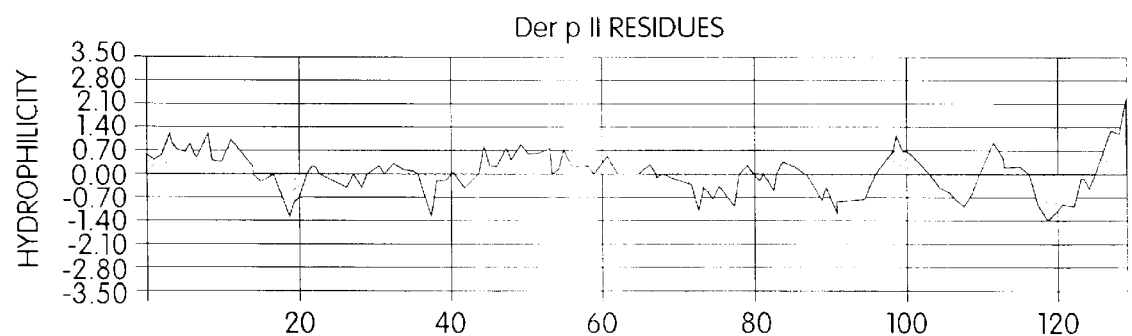

FIGS. 17A and 17B is a hydrophilicity plot of *Der f* II and *Der p* II using the Hopp-Woods algorithm computed with the Mac Vector Sequence Analysis Software (IBI, New Haven) using a 6-residue window.

FIG. 18 is a composite alignment of the amino acid sequences of five *Der p* I clones (a)–(e) which illustrates polymorphism in the *Der p* I protein. The numbering refers to the sequence of the *Der p* I(a) clone. The symbol (–) is used to indicate that the amino acid residue of a *Der p* I clone is identical to the corresponding amino acid residue of *Der p* I(a) at that position. The amino acid sequences of these clones indicate that there may be significant variation in *Der p* I, with five polymorphic amino acid residues found in the five sequences.

FIG. 19 is a composite alignment of the amino acid sequences of three *Der p* II clones (c), (1) and (2) which illustrates polymorphism in the *Der p* II protein. The numbering refers to the sequence of the *Der p* II(c) clone. The symbol (.) is used to indicate that the amino acid residue of a *Der p* II clone is identical to the corresponding amino acid residue of *Der p* II (c) at that position.

FIG. 20 is a composite alignment of the amino acid sequences of six *Der f* II clones (i.e., pFL1, pFL2, MT3, MT5, MT18 and MT16) which illustrates polymorphism in the *Der f* II protein. The numbering refers to the sequences of the *Der f* pFL1 clone. The symbol (.) is used to indicate that the amino acid residue of a *Der f* II clone is identical to the corresponding amino acid residue of *Der f* II pFL1 at that position.

FIGS. 21A, 21B and 21C is the nucleotide and predicted amino acid sequences of cDNA λgt11 p1(13T), including the full length of the preproenzyme form of Der p I. Negative sequence numbers refer to the proposed pre- and preproenzyme forms of Der p I.

DETAILED DESCRIPTION OF THE INVENTION

The present invention relates to a nucleotide sequence coding for an allergen from the house dust mite Dermatophagoides and to the encoded Dermatophagoides protein or peptide which includes at least one epitope of the Dermatophagoides allergen. It particularly relates to a nucleotide sequence capable of expression in an appropriate host of a major allergen of D. farinae, such as Der f I or Der f II, or of a peptide which includes at least one epitope of Der f I or of Der f II. It also particularly relates to a nucleotide sequence capable of expression in an appropriate host of a major allergen of D. pteronyssinus, such as Der p I or Der p II, or of a peptide which includes at least one epitope of Der p I or of Der p II. The Dermatophagoides nucleotide sequence is useful as a probe for identifying additional nucleotide sequences which hybridize to it and encode other mite allergens, particularly D. farinae or D. pteronyssinus allergens. Further, the present invention relates to nucleotide sequences which hybridize to a D. farinae protein-encoding nucleotide sequence or a D. pteronyssinus protein-encoding nucleotide sequence but which encode a protein from another species or type of house dust mite, such as D. microceras (e.g., Der m I and Der m II).

The encoded Dermatophagoides mite allergen or peptide which includes at least one Dermatophagoides (Der f I or Der f II; Der p I or Der p II) epitope can be used for diagnostic purposes (e.g., as an antigen) and for therapeutic purposes (e.g., to desensitize an individual). Alternatively, the encoded house dust mite allergen can be a protein or peptide, such as a D. microceras protein or peptide, which displays the antigenicity of or is cross-reactive with a Der f or a Der p allergen; generally, these have a high degree of amino acid homology.

Accordingly, the present invention also relates to compositions which include a Dermatophagoides allergen (e.g., Der f I allergen, Der f II allergen; Der p I or Der p II allergen or other D. allergen cross-reactive therewith) or a peptide which includes at least one epitope of a Dermatophagoides allergen (Der f I, Der f II, Der p I, Der p II or other D allergen cross-reactive therewith) individually or in combination, and which can be used for therapeutic applications (e.g., desensitization). As is described below, DNA coding for major allergens from house dust mites have been isolated and sequenced. In particular, and as is described in greater detail in the Examples, cDNA clones coding for the Der p I, Der p II, Der f I and Der f II allergens have been isolated and sequenced. The nucleotide sequence of each of these clones has been compared with that of the homologous allergen from the related mite species (i.e., Der p I and Der f I; Der p II and Der f II), as has the predicted amino acid sequence of each.

The following is a description of isolation and sequencing of the two cDNA clones coding for Der f allergens and their comparison with the corresponding D. pteronyssinus allergen and a description of use of the nucleotide sequences and encoded products in a diagnostic or a therapeutic context.

Isolation and Sequence Analysis of Der f I

A cDNA clone coding for Der f I, a major allergen from the house dust mite D. farinae, has been isolated and sequenced. A restriction map of the cDNA insert of the clone is represented in FIG. 9, as is the strategy of DNA sequencing. This Der f I cDNA clone contains a 1.1-kb cDNA insert encoding a typical signal peptide, a proenzyme region and the mature Der f I protein. The product is 321 amino acid residues; a putative 18 residue signal peptide, an 80 residue proenzyme (pro-peptide) region, and a 223 residue mature enzyme region. The derived molecular weight is 25,191. The nucleotide sequence and the predicted amino acid sequence of the Der f I cDNA are represented in FIG. 10. The deduced amino acid sequence shows significant homology to other cysteine proteases in the pro-region, as well as in the mature protein. Sequence alignment of the mature Der f I protein with the homologous allergen Der p I from the related mite D. pteronyssinus (FIG. 11) revealed a high degree of homology (81%) between the two proteins, as predicted by previous sequencing at the protein level. In particular, the residues comprising the active site of these enzymes were conserved and a potential N-glycosylation site was present at equivalent positions in both mite allergens.

Conserved cysteine residue pairs (31, 71) and (65, 103), where the numbering refers to Der p I, are apparently involved in disulphide bond formation on the basis of the assumed similarity of the three dimensional structure of Der p I and Der f I to that of papain and actinidin, which also have an additional disulphide bridge. The fifth and final cysteine residue for which there is a homologous cysteine residue in papain and actinidin is the active site cysteine (residue 35 in Der f I). It is not unlikely that the two extra cysteine residues present in Der p I and Der f I may be involved in forming a third disulphide bridge.

The potential N-glycosylation site in Der p I is also present at the equivalent position in Der f I, with conservation of the crucial first and last residues of the tripeptide site. The degree of glycosylation of Der f I and Der p I has yet to be determined. Carbohydrates, including mannose, galactose, N-acetylglucosamine and N-acetylgalactosamine, have been reported in purified preparations of these mite allergens (Chapman, M. D., J. Immunol., 12:587–592 (1980); Wolden, S. et al., Int. Arch. Allergy Appl. Immunol., 68:144–151 (1982)).

Given the degree of homology over the first thirty N-terminal amino acid residues between mature Der p I and Der m I (70%) and mature Der f I and Der m I (97%) with the Der m I residues determined by conventional amino acid sequencing (Platts-Mills TAE et al., In: Mite Allergy, a World-Wide Problem, 27–29 (1988); Lind, P. and N. Horn, In: Mite Allergy, a World-Wide Problem, 30–34 (1988)), it is probable that the full mature Der m I sequence will confirm an overall 70–80% homology between the Group I mite allergens. Der m I is an allergen from D. microceras. High homology between the proenzyme moieties of Der p I and Der f I (91%) over the residues −23 to −1 and the structural analysis of Der f I suggests that the Group I allergens are likely to have N-terminal extension peptides of the mature protein of homologous structure and, at least for the propeptide, composition.

Studies on the fine structure of the design of signal sequences have identified three structurally dissimilar regions so far: a positively charged N-terminal (n) region, a central hydrophobic (h) region and a more polar C-terminal (c) region that seems to define the cleavage site (Von Heijne, G., EMBO J., 3:2315–2323 (1984); Eur. J. Biochem., 133:17–21 (1983); J. Mol. Biol., 184:99–105 (1985)). Analysis of the signal peptide of Der f I revealed that it, too, contained these regions (FIG. 12). The n-region is extremely variable in length and composition, but its net charge does not vary appreciably with the overall length, and has a mean value of about +1.7. The n-region of the *Der f* I signal peptide, with a length of two residues, has a net charge of +2 contributed by the initiator methionine (which is unformylated and hence positively charged in eukaryotes) and the adjacent lysine (Lys) residue. The h-region of *Der f* I is enriched with hydrophobic residues, the characteristic feature of this region, with only one hydrophilic residue serine (Ser) present which can be tolerated. The overall amino acid composition of the *Der f* I c-region is more polar than that of the h-region as is found in signal sequences with the h/c boundary located between residues −6 and −5, which is its mean position in eukaryotes. Thus, the *Der f* I pre-peptide sequence appears to fulfill the requirements to which a functional signal sequence must conform.

While the signal sequence of *Der f* I and other cysteine proteases share structural homology, all being composed of the n,h and c-regions, they are highly variable with respect to overall length and amino acid sequence, as is clear in FIG. 12. However, significant sequence homology has been shown between the pro-regions of cysteine protease precursors (Ishidoh, K. et al., *FEBS Letters,* 226:33–37 (1987)). Alignment of the proenzyme regions of *Der f* I and a number of other cysteine proteases (FIG. 12) indicated that these proregions share a number of very conserved residues as well as semi-conserved residues which were present in over half of the sequences. This homology was increased if conservative amino acids such as valine (Val), isoleucine (Ile) and leucine (Leu) (small hydrophobic residues) or arginine (Arg) and Lys (positively charged residues) were regarded as identical. The *Der f* I proregion possessed six out of seven highly conserved amino acids and all the residues at sites of conservative changes. The homology at less conserved sites was lower. Homology in the pro-peptide, in particular the highly conserved residues, may be important when considering the function of the pro-peptide in the processing of these enzymes, since it indicates that these sequences probably have structural and functional similarities.

Highly cross-reactive B cell epitopes on *Der f* I and *Der p* I have been demonstrated using antibodies present in mouse, rabbit and human sera (Heymann, P. W. et al., *J. Immunol.* 137:2841–2847 (1986); Platts-Mills, TAE et al.,*J. Allergy Clin. Immunol.* 78:398–407 (1986)). However, species-specific epitopes have also been defined in these systems. Murine monoclonal antibodies bound predominantly to species-specific determinants (Platts-Mills TAE et al.,*J. Allergy Clin. Immunol.* 139:1479–1484 (1987)). Some 40% of rabbit anti-*Der p* I reactivity was accounted for by epitopes unique to *Der p* I (Platts-Mills, TAE et al., *J. Allergy Clin. Immunol,* 78:398–407 (1986)), and some species-specific binding of antibodies from allergic humans was observed, although the majority bind to cross-reactive epitopes (Platts-Mills TAE et al., *J. Immunol.* 139:1479–1484 (1987)).

The recombinant DNA strategy of gene fragmentation and expression was used (Greene, W. K. et al., *Immunol. (*1990)) to define five antigenic regions of recombinant *Der p* I which contained B cell epitopes recognized by a rabbit anti-*Der p* I antiserum. Using the technique of immunoabsorption, three of these putative epitopes were shown to be shared with *Der f* I (located on regions containing amino acid residues 34-47, 60-72 and 166-194) while two appeared to be specific for *Der p* I (regions 82–99 and 112–140). Differences in the reactivity of these peptides to rabbit anti-*D. farinae* supported the above division into cross-reactive and species-specific epitopes. The sequence differences shown between the *Der p* I and the *Der f* I proteins are primarily located in the N and C terminal regions, as well as in an extended surface loop (residues 85-136) linking the two domains of the enzyme that includes helix D (residues 127-136), as predicted from the secondary and tertiary structures of papain and actinidin (Baker, E. N. and J. Drenth, In: *Biological Macromolecules and Assemblies,* Vol. 3, pp. 314–368, John Wiley and Sons, NY (1987)). The surface location of these residues is supported by the hydrophilicity plots of *Der p* I and *Der f* I in FIG. 13, which illustrate the predominantly hydrophilic nature of this region that predicts surface exposure. This region also contains the two species-specific B cell epitopes recognized by the rabbit anti-*Der p* I serum (see above). Analysis of the sequences in the regions containing the cross-reactive epitopes (located in regions 34–47 and 60–72) are completely conserved between *Der p* I and *Der f* I, while the majority of residues in a third cross-reactive epitope-containing region (residues region 166–194) were conserved.

Expression of cDNA encoding *Der f* I results in production of pre-pro-*Der f* I protein in *E. coli,* a recombinant protein of greater solubility, stability and antigenicity than that of recombinant *Der p* I. Protein encoded by *Der f* I cDNA has been expressed using a pGEX vector and has been shown by radioimmune assay to react with rabbit anti-*D farinae* antibodies. The availability of high yields of soluble *Der f* I allergen and antigenic derivatives will facilitate the development of diagnostic and therapeutic agents and the mapping of B and T cell antigenic determinants.

With the availability of the complete amino acid sequence of recombinant *Der f* I, mapping of the epitopes recognized by both the B and T cell compartments of the immune system can be carried out. The use of techniques such as the screening of overlapping synthetic peptides, the use of monoclonal antibodies and gene fragmentation and expression should enable the identification of both the continuous and topographical epitopes of *Der f* I. It will be particularly useful to determine whether allergenic (IgE-binding) determinants have common features and are intrinsically different from antigenic (IgG-binding) determinants and whether T cells recognize unique epitopes different from those recognized by B cells. Studies to identify the *Der f* I epitopes reactive with mite allergic human IgE antibodies and the division of these into determinants cross-reactive with *Der p* I and determinants unique to *Der f* I can also be carried out. B cell (and T cell) epitopes specific for either species can be used to provide useful diagnostic reagents for determining reactivity to the different mite species, while cross-reacting epitopes are candidates for a common immunotherapeutic agent.

As described in detail in the Examples, a cDNA clone coding for *Der p* I which contained a 0.8-kb cDNA insert has been isolated. Sequence analysis revealed that the 222 amino acid residue mature recombinant *Der p* I protein showed significant homology with a group of cysteine proteases, including actinidin, papain, cathepsin H and cathepsin B.

Isolation and Sequence Analysis of *Der f* II

A cDNA clone coding for *Der f* II, a major allergen from the house dust mite *D. farinae,* has been isolated and sequenced, as described in the Examples. The nucleotide sequence and the predicted amino acid sequence of the *Der f* II cDNA are represented in FIG. 14. A restriction map of the cDNA insert of a clone coding for *Der f* II is represented in FIG. 15.

FIG. 16 shows the alignment of *Der f* II and *Der p* II cDNA sequences. The homology of the sequence of *Der f* II with *Der p* II (88%) is higher than the 81% homology found with *Der p* I and *Der f* I, which is significantly different (p<0.05) using the chi$^2$ distribution. The reason for this may simply be that the Group I allergens are larger and each residue may be less critical for the structure and function of the molecule. It is known, for example, that assuming they adopt a similar conformation to other cysteine proteases, many of the amino acid differences in *Der p* I and *Der f* I lie in residues linking the two domain structures of the molecules. The 6 cysteine molecules are conserved between the group II allergens, suggesting a similar disulphide bonding, although this may be expected, given the high overall homology. Another indication of the conservation of these proteins is that 34/55 of the nucleotide changes of the coding sequence are in the third base of a codon, which usually does not change the amino acid. Residues that may be of importance in the function of the molecule are Ser 57 where all three bases are changed but the amino acid is conserved. A similar phenomenon exists at residue 88, where a complete codon change has conserved a small aliphatic residue. Again, like *Der p* II, the *Der f* II cDNA clone does not have a poly A tail, although the 3' non-coding region is rich in adenosine and has two possible polyadenylation signals ATAA. The nucleotides encoding the first four residues are from the PCR primer which was designed from the known homology of *Der p* II and *Der f* II from N-terminal amino acid sequencing. A primer based on the C-terminal sequence can now be used to determine these bases, as well as the signal sequence.

Uses of the subject allergenic proteins/peptides and DNA encoding same

The materials resulting from the work described herein, as well as compositions containing these materials, can be used in methods of diagnosing, treating and preventing allergic responses to mite allergens, particularly to mites of the genus Dermatophagoides, such as *D. farinae* and *D pteronyssinus*. In addition, the cDNA (or the mRNA from which it was transcribed) can be used to identify other similar sequences. This can be carried out, for example, under conditions of low stringency and those sequences having sufficient homology (generally greater than 40%) can be selected for further assessment using the method described herein. Alternatively, high stringency conditions can be used. In this manner, DNA of the present invention can be used to identify sequences coding for mite allergens having amino acid sequences similar to that of *Der f* I, *Der f* II, *Der p* I or *Der p* II. Thus, the present invention includes not only *D. farinae* and *D. pteronyssinus* allergens, but other mite allergens as well (e.g., other mite allergens encoded by DNA which hybridizes to DNA of the present invention).

Proteins or peptides encoded by the cDNA of the present invention can be used, for example, as "purified" allergens. Such purified allergens are useful in the standardization of allergen extracts or preparations which can be used as reagents for the diagnosis and treatment of allergy to house dust mites. Through use of the peptides of the present invention, allergen preparations of consistent, well-defined composition and biological activity can be made and administered for therapeutic purposes (e.g., to modify the allergic response of a house dust mite-sensitive individual). *Der f* I or *Der f* II peptides or proteins (or modified versions thereof, such as are described below) may, for example, modify B-cell response to *Der f* I or *Der f* II, T-cell response to *Der f* I and *Der f* II, or both responses. Similarly, *Der p* I or *Der p* II proteins or peptides may be used to modify B-cell and/or T-cell response to *Der p* I or *Der p* II. Purified allergens can also be used to study the mechanism of immunotherapy of allergy to house dust mites, particularly to *Der f* I, *Der f* II, *Der p* I and *Der p* II, and to design modified derivatives or analogues which are more useful in immunotherapy than are the unmodified ("naturally-occurring") peptides.

In those instances in which there are epitopes which are cross-reactive, such as the three epitopes described herein which are shared by *Der f* I and *Der p* I, the area(s) of the molecule which contain the cross-reactive epitopes can be used as common immunotherapeutic peptides to be administered in treating allergy to the two (or more) mite species which share the epitope. For example, the cross-reactive epitopes could be used to induce IgG blocking antibody against both allergens (e.g., *Der f* I and *Der p* I allergen). A peptide containing a univalent antibody epitope can be used, rather than the entire molecule, and may prove advantageous because the univalent antibody epitope cannot crosslink mast cells and cause adverse reactions during desensitizing treatments. It is also possible to attach a B cell epitope to a carrier molecule to direct T cell control of allergic responses.

Alternatively, it may be desirable or necessary to have peptides which are specific to a selected Dermatophagoides allergen. As described herein, two epitopes which are apparently *Der p* I-specific have been identified. A similar approach can be used to identify other species-specific epitopes (e.g., *Der p* I or II, *Der f* I or II). The presence in an individual of antibodies to the species-specific epitopes can be used as a quick serological test to determine which mite species is causing the allergic response. This would make it possible to specifically target therapy provided to an individual to the causative species and, thus, enhance the therapeutic effect.

Work by others has shown that high doses of allergens generally produce the best results (i.e., best symptom relief). However, many people are unable to tolerate large doses of allergens because of allergic reactions to the allergens. Modification of naturally-occurring allergens can be designed in such a manner that modified peptides or modified allergens which have the same or enhanced therapeutic properties as the corresponding naturally-occurring allergen but have reduced side effects (especially anaphylactic reactions) can be produced. These can be, for example, a peptide of the present invention (e.g., one having all or a portion of the amino acid sequence of *Der f* I or *Der f* II, *Der p* I or *Der p* II). Alternatively, a combination of peptides can be administered. A modified peptide or peptide analogue (e.g., a peptide in which the amino acid sequence has been altered to modify immunogenicity and/or reduce allergenicity or to which a component has been added for the same purpose) can be used for desensitization therapy.

Administration of the peptides of the present invention to an individual to be desensitized can be carried out using known techniques. A peptide or combination of different peptides can be administered to an individual in a composition which includes, for example, an appropriate buffer, a carrier and/or an adjuvant. Such compositions will generally be administered by injection, inhalation, transdermal application or rectal administration. Using the information now available, it is possible to design a *Der p* I, *Der p* II, *Der f* I or *Der f* II peptide which, when administered to a sensitive individual in sufficient quantities, will modify the individual's allergic response to *Der p* I, *Der p* II, *Der f* I and/or *Der f* II. This can be done, for example, by examining the structures of these allergens, producing peptides to be examined for their ability to influence B-cell and/or T-cell responses in house dust mite-sensitive individuals and selecting appropriate epitopes recognized by the cells. Synthetic amino acid sequences which mimic those of the epitopes and which are capable of down regulating allergic response to *Der p* I, *Der p* II, *Der f* I or *Der f* II allergens can be made. Proteins, peptides or antibodies of the present invention can also be used, in known methods, for detecting and diagnosing allergic response to *Der f* I or *Der f* II. For example, this can be done by combining blood obtained from an individual to be assessed for sensitivity to one of these allergens with an isolated allergenic peptide of house dust mite, under conditions appropriate for binding of or stimulating components (e.g., antibodies, T cells, B cells) in the blood with the peptide and determining the extent to which such binding occurs. *Der f* and *Der p* proteins or peptides can be administered together to treat an individual sensitive to both allergen types.

It is now also possible to design an agent or a drug capable of blocking or inhibiting the ability of *Der p* I, *Der p* II, *Der f* I or *Der f* II to induce an allergic reaction in house dust mite-sensitive individuals. Such agents could be designed, for example, in such a manner that they would bind to relevant anti-*Der p* I, anti-*Der p* II, anti-*Der f* I or anti-*Der f* II IgEs, thus preventing IgE-allergen binding and subsequent mast cell degranulation. Alternatively, such agents could bind to cellular components of the immune system, resulting in suppression or desensitization of the allergic response to these allergens. A non-restrictive example of this is the use of appropriate B- and T-cell epitope peptides, or modifications thereof, based on the cDNA/protein structures of the present invention to suppress the allergic response to these allergens. This can be carried out by defining the structures of B- and T-cell epitope peptides which affect B- and T-cell function in in vitro studies with blood cells from house dust mite-sensitive individuals.

The cDNA encoding *Der p* I, *Der p* II, *Der f* I or *Der f* II or a peptide including at least one epitope thereof can be used to produce additional peptides, using known techniques such as gene cloning. A method of producing a protein or a peptide of the present invention can include, for example, culturing a host cell containing an expression vector which, in turn, contains DNA encoding all or a portion of a selected allergenic protein or peptide (e.g., *Der p* I, *Der p* II, *Der f* I, *Der f* II or a peptide including at least one epitope). Cells are cultured under conditions appropriate for expression of the DNA insert (production of the encoded protein or peptide). The expressed product is then recovered, using known techniques. Alternatively, the allergen or portion thereof can be synthesized using known mechanical or chemical techniques. As used herein, the term protein or peptide refers to proteins or peptides made by any of these techniques. The resulting peptide can, in turn, be used as described previously.

DNA to be used in any embodiment of this invention can be cDNA obtained as described herein or, alternatively, can be any oligodeoxynucleotide sequence having all or a portion of the sequence represented in FIGS. 1, 7, 10 and 14 or their functional equivalent. Such oligodeoxynucleotide sequences can be produced chemically or mechanically, using known techniques. A functional equivalent of an oligonucleotide sequence is one which is capable of hybridizing to a complementary oligonucleotide sequence to which the sequence (or corresponding sequence portions) of FIGS. 1, 7, 10 and 14 hybridizes and/or which encodes a product (e.g., a polypeptide or peptide) having the same functional characteristics of the product encoded by the sequence (or corresponding sequence portion) represented in these figures. Whether a functional equivalent must meet one or both criteria will depend on its use (e.g., if it is to be used only as an oligoprobe, it need meet only the first criterion and if it is to be used to produce house dust mite allergen, it need only meet the second criterion).

The structural information now available (e.g., DNA, protein/peptide sequences) can also be used to identify or define T cell epitope peptides and/or B cell epitope peptides which are of importance in allergic reactions to house dust mite allergens and to elucidate the mediators or mechanisms (e.g., interleukin-2, interleukin-4, gamma interferon) by which these reactions occur. This knowledge should make it possible to design peptide-based house dust mite therapeutic agents or drugs which can be used to modulate these responses.

The present invention will now be further illustrated by the following Examples, which are not intended to be limiting in any way.

EXAMPLE 1

MATERIALS AND METHODS

Cloning and Expression of *Der p* I cDNA

Polyadenylated mRNA was isolated from the mite Dermatophagoides pteronyssinus cultured by Commonwealth Serum Laboratories, Parkville, Australia, and cDNA was synthesized by the RNA-ase H method (5) using a kit (Amersham, International, Bucks). After the addition of EcoRI linkers the cDNA was ligated into λgt11 and plated in *E. coli* Y1090 (r−) (Promega Biotec, Madison, Wis.), to produce a library of $5\times10^5$ recombinants. Screening was performed by plaque radioimmune assay (6) using a rabbit anti-*Der p* I antiserum (7). Reactivity was detected by hydrochloride in 0.1M sodium acetate buffer pH 5.2 were then added and the mixture was homogenized and spun at 10,000 rpm for 30 min in a Sorval SS34 rotor. The supernatant was collected and layered onto a CsCl pad (5 ml of 4.8M CsCl in 10 mM EDTA) and centrifuged at 37,000 rpm for 16 h at 15° C. in a SW41 TI rotor (Beckman Instruments, Inc., Fullerton, Calif.). The DNA band at the interphase was collected and diluted 1:15 in 10 mM Tris HCl/1 mM EDTA buffer, pH 8.0. Banding of genomic DNA in CsCl was carried out by the standard method.

Isolation of DNA from λgt11 p1 cDNA Clone

Phage DNA from λgt11 p1 clone was prepared by a rapid isolation procedure. Clarified phage plate lysate (1 ml) was mixed with 270 μl of 25% wt/vol polyethylene glycol (PEG 6000) in 2.5M NaCl and incubated at room temperature for 15 min. The mixture was then spun for 5 min in a microfuge (Eppendorf, Federal Republic of Germany), and the supernatant was removed. The pellet was dissolved in 100 μl of 10 mM Tris/HCl pH 8.0 containing 1 mM EDTA and 100 mM NaCl. This DNA preparation was extracted 3 times with phenol/chloroform (1:1) and the DNA was precipitated by ethanol.

DNA Hybridization

Nucleic acid was radiolabelled with $^{32}P$ by nick translation (10). DNA samples were digested with appropriate restriction enzymes using conditions recommended by the supplier. Southern blots were prepared using Zeta-Probe membranes (Bio-Rad Laboratories, Richmond, Calif.). Prehybridization, hybridization, posthybridization washes were carried out according to the manufacturers recommendations (bulletin 1234, Bio-Rad Laboratories).

Cloning and DNA Sequencing

To clone the 0.8-kb cDNA insert from clone λgt11 p1 into plasmid pUC8, phage DNA was digested with EcoRI restriction enzyme and then ligated to EcoRI-digested pUC8 DNA and used to transform *Escherichia coli* JM83. The resulting recombinant plasmid was designated as pHDM 1.

To obtain clones for DNA sequence analysis, the cDNA insert was isolated from pHDM 1 and ligated to M13- derived sequencing vectors mp18 and mp19 (16). Transformation was carried out using *E coli* JM107 and sequencing was performed by the dideoxynucleotide chain termination method (11).

RESULTS

Figure 2:
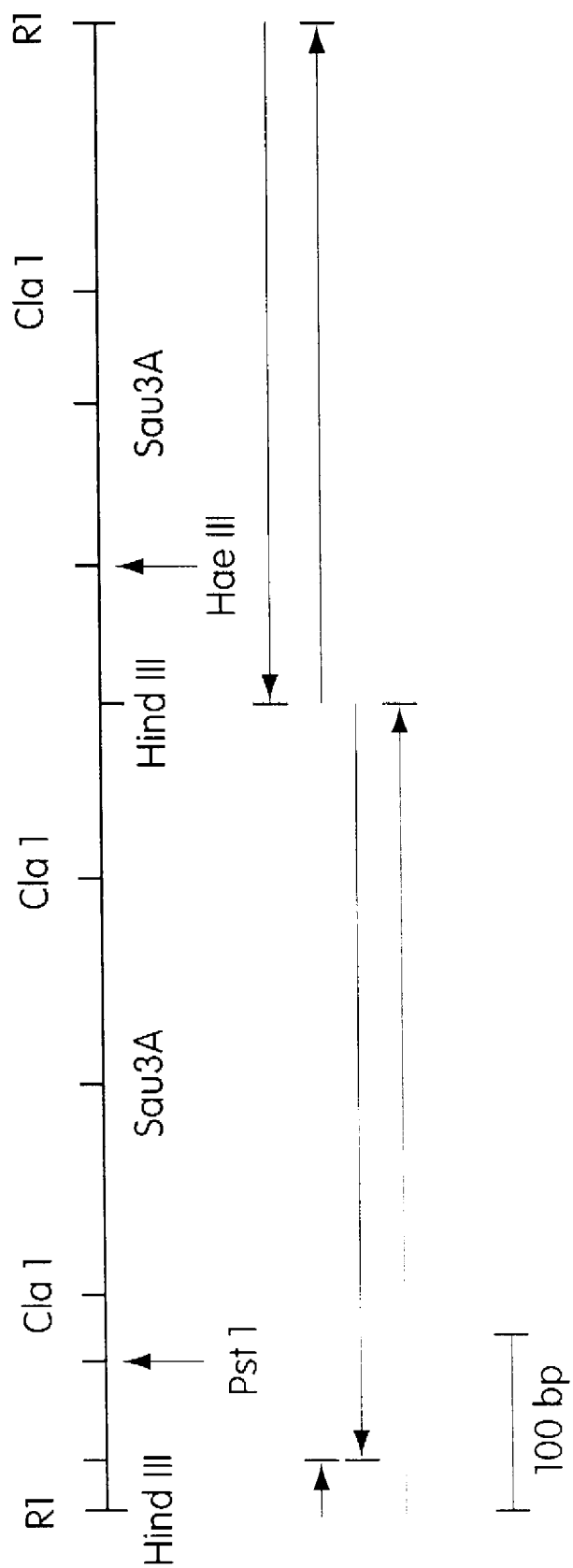
FIG. 2 shows the restriction map of the cDNA insert of clone λgt11 p1(13T) and the strategy of DNA sequencing. Arrows indicate directions in which sequences were read.

Several phage clones reacted with the rabbit anti *Der p* I serum and hybridized with all 3 oligonucleotide probes. One of these, λgt11 p1(13T), was examined further. The nucleotide sequence of the cDNA insert from this clone, λgt11 p1, was determined using the sequencing strategy shown in FIG. 2. The complete sequence was shown to be 857 bases long and included a 69-base-long 5' proximal end sequence, a coding region for the entire native *Der p* I protein of 222 amino acids with a derived molecular weight of 25,371, an 89-base-long 3' noncoding region and a poly (A) tail of 33 residues (FIG. 1).

The assignment of a threonine residue at position 1 as the $NH_2$-terminal amino acid of *Der p* I was based on data obtained by $NH_2$-terminal amino acid sequencing of the pure protein isolated from mite excretions (17). The predicted amino acid sequence matched with data obtained by amino acid sequence analysis of the $NH_2$-terminal region as well as with internal sequences derived from analyses of tryptic peptides (FIG. 1). The complete mature protein is coded by a single open reading frame terminating at the TAA stop codon at nucleotide position 736-738. At present, it is not certain whether the first ATG codon at nucleotide position 16-18 is the translation initiation site, since the immediate flanking sequence of this ATG codon (TTGATGA) showed no homology with the Kozak consenses sequence (ACCATGG) for the eukaryotic translation initiation sites (18). In addition, the 5' proximal end sequence does not code for a typical signal peptide sequence (see below).

The amino acid sequence predicted by nucleotide analysis is shown in FIG. 1. A protein data-base search revealed that the *Der p* I amino acid sequence showed homology with a group of cysteine proteases. Previous cDNA studies have shown that lysosomal cathepsins B, a mouse macrophage protease and a cysteine protease from an amoeba have transient pre- and proform intermediates (19–21), and inspection of the amino acid sequence at the 5' proximal end of the λgt11 p1 cDNA clone suggests that *Der p* I may be similar. First, the hydrophilicity plot (22) of the sequence preceding the mature protein sequence lacks the characteristic hydrophobic region of a signal peptide (23) and second, an Ala-X-Ala sequence, the most frequent sequence preceding the signal peptidase cleavage site (24,25), is present at positions −13, −14, −15 (FIG. 1). Therefore, it is proposed that cleavage between pro-*Der p* I sequence and the pre-*Der p* I sequence occurs between Ala (−13) and Phe (−12). Thus, pro-*Der p* I sequence begins at residues Phe (−12) and ends at residues Glu (−1). The amino acids residues numbered −13 to −23 would then correspond to a partial signal peptide sequence. The full length of the *Der p* I preproenzyme sequence has been determined and is shown in FIG. 21. The negative sequence numbers refer to the pre- and preproenzyme forms of *Der p* I.

When the 857-bp cDNA insert was radiolabelled and hybridized against a Southern blot of EcoRI-digested genomic DNA from house dust mite, hybridization to bands of 1.5, 0.5, and 0.35 kb was observed (data not shown). As shown in the restriction enzyme map of the cDNA insert (FIG. 2), there was no internal EcoRI site and the multiple hybridization bands observed suggest that *Der p* I is coded by a noncontiguous gene. The results also showed little evidence of gene duplication since hybridization was restricted to fragments with a total length of 2.4 kb.

The N-terminal can be compared with N-terminal of the equivalent protein from *D. farinae* (*Der f* I) (12). There is identity in 11/20 positions of the sequences available for comparison (FIG. 3).

To examine the protein produced by λgt11 p1(13T), phage was lysogenized in Y1089 (r−) and the bacteria grown in broth culture at 30° C. Phage was induced by temperature switch and isopropyl thiogalactopyranoside (IPTG) (6) and the bacteria were suspended in PBS to 1/20 of the culture volume, and sonicated for an antigen preparation. When examined by 7.5% SDS-PAGE electrophoresis it was found that λgt11 p1(13T) did not produce a Mr 116K β-galactosidase band but instead produced a 140K band consistent with a fusion protein with the *Der p* I contributing a 24 kDa moiety (6). Rabbit anti *Der P* I was shown to react with the lysate from λgt11 p1(13T) (FIG. 4).

EXAMPLE 2

Expression of *Der p* I cDNA products reactive with IgE from allergic serum

The DNA insert from λgt11 p1(13T) which codes for *Der p* I was subcloned into the EcoRI site of the plasmid expression vector (pGEX)(26) where it could be expressed as a fusion with a glutathione transferase molecule. *E coli* infected with this plasmid pGEX-p1(13T) or with the vector alone were grown to a log phase culture and harvested by centrifugation. The bacteria were suspended in PBS to 1/20 of their culture volume and lysed by freeze-thawing. The lysate was shown by sodium dodecyl-sulphate polyacrylamide electrophoresis to express a fusion protein in high concentration of the expected Mr 50,000. These lysates were then tested for their ability to react with IgE from allergic serum by radioimmune dot-blot conducted by the method described by Thomas and Rossi (27). The serum was taken from donors known to be mite-allergic or from non-allergic controls. Reactivity was developed by $^{125}$I-monoclonal anti-IgE and autoradiography. FIG. 5 shows the lysate from pGEX-p1(13T), but not the vector control reacted with IgE in allergic serum, but not non allergic serum.

EXAMPLE 3

Inhibition of IgE antibody responses to *Der p* I by treatment with the product from a cDNA clone coding for *Der p* I

*E. coli* lysogenized by λgt11 p1(13T) were grown and induced by temperature switch to produce a recombinant fusion protein which was consistent with a 24 kD *Der p* I moiety and a 116 kD β-galactosidase moiety (p1(13T) (28). This protein was mostly insoluble and could be isolated to about 90% purity, judged by sodium didodecyl polyacrylamide electrophoresis, by differential centrifugation. A similar protein was produced from another gt11 cDNA mite clone λgt pX (2c). To test for the ability of the recombinant protein to modify IgE antibody responses to *Der p* I, groups of 4–5 CBA mice were injected intraperitoneally with 2 mg of the p1(13T) or pX (2c) fusion proteins and after 2 days given a subcutaneous injection of 5 μg of native *Der p* I (from mite culture medium) in aluminium hydroxide gel. The IgE antibody titres were measured by passive cutaneous anaphylaxis (PCA) after 3 and 6 weeks. The methods and background data for these responses have been described by Stewart and Holt (29). For a specificity control, groups of mice injected with p1(13T) or pX (2c) were also injected with 10 μg of ovalbumin in alum. Responses were compared to mice without prior p1(13T) or pX (2c) treatment (Table 1). After 3 weeks mice either not given an injection of recombinant protein or injected with the control pX (2c) had detectable anti *Der p* I PCA titres (½ or greater). Only ⅕ of mice treated with recombinant p1(13T) had a detectable titre and this at ¼ was lower than all of the titres of both control groups. Titres of all groups at 6 weeks were low or absent (not shown). The PCA response to ovalbumin was not significantly affected by treatment with recombinant proteins. These data show the potential of the recombinant proteins to specifically decrease IgE responses as required for a desensitizing agent.

TABLE 1

Inhibition of anti-Der p I IgE by preinjection with with recombinant Der p I.

| group | preinjection −2 days | immunizing injection (d0) (5 μg/alum) | IgE (PCA) titres at d21 responders | titres |
|---|---|---|---|---|
| 1 | — | Der p I | 4/4 | 1/16–1/64 |
| 2 | pX(2C) | Der p I | 5/5 | 1/8–1/16 |
| 3 | p1(13T) | Der p I | 1/5* | 1/4* |
| 4 | — | ovalbumin | 4/4 | 1/64–1/256 |
| 5 | pX(2C) | ovalbumin | 5/5 | 1/32–1/128 |
| 6 | p1(13T) | ovalbumin | 5/5 | 1/64–1/256 |

*Mann Whitney analysis.

Mice were given a preinjection on day −2 and then immunized with *Der p* I or ovalbumin on day 0. Serum antibody titres were measured on day 21 and 42 by PCA in rat skin. Significant anti-*Der p* I titres were not detected on day 42 (not shown). The PCA were measured to *Der p* I for groups 1–3 and ovalbumin for groups 4–6. The anti-*Der p* I titres were lower (p<0.001)* when pretreated with recombinant *Der p* I p1(13T).
*Mann Whitney analysis.

EXAMPLE 4
Expression of *Der p* I antigenic determinants by fragments of the cDNA from λgt11 p1(13T)

The cDNA from λgt11 (13T) coding for *Der p* I was fragmented by sonication. The fragments (in varying size ranges) were isolated by electrophoresis, filled in by the Klenow reaction to create blunt ends. EcoRI linkers were attached and the fragment libraries cloned in λgt11. The methods used for the fragments cloning were the same as that used for cDNA cloning (6). Plaque immunoassay was used for screening with rabbit anti-*Der p* I. Three phage clones reacting with the antiserum were isolated and the oligonucleotide sequences of the cloned fragments obtained. Two of these were found to code for *Der p* I amino acids 17-55 (see FIG. 1 for numbering) and one for amino acids 70-100. Such fragments will eventually be useful for both diagnostic reagents to determine epitope reactivity and for therapy where molecules of limited allergenicity may increase safety of desensitisation.

EXAMPLE 5
Cloning and expression of cDNA coding for the major mite allergen *Der p* II The *Dermatophagoides pteronyssinus* cDNA library in λgt11 previously described was screened by plaque radio-immune assay using nitrocellulose lifts (6). Instead of using specific antisera the sera used was from a person allergic to house dust mites. The serum (at ½ dilution) was absorbed with *E. coli*. To detect reactivity an $^{125}$I labelled monoclonal anti-IgE was used (at 30 ng/ml with 2×10$^6$ cpm/ml (approx. 30% counting efficiency)). After 1 hour the filters were washed and autoradiography performed. Using this procedure 4 clones reacting with human IgE were isolated. It was found they were related by DNA hybridization and had an identical pattern of reactivity against a panel of allergic sera. FIG. 6 shows IgE reactivity in plaque radioimmunoassay against allergic serum (AM) (top row) or non allergic (WT). Here, clones 1, 3 and 8 react strongly, but only against allergic sera. The amp 1 segments (present in row 1) are a λgt11 vector control. The bottom row is an immunoassay with rabbit anti-*Der p* I, developed by $^{125}$I staphylococcus protein A which shows no significant reactivity. The clones were tested against a panel of sera. Serum from five patients without allergy to mite did not react, but serum from 14/17 people with mite allergy showed reactivity. The DNA insert from the clone λgt11 pII(C1) was subcloned into M13 mp18 and M13 mp19 and sequenced by the chain termination method. The nucleotide sequence (FIG. 7) showed this allergen was *Der p* II by (a) the homology of the inferred amino acid sequence of residues 1-40 with that of the N-terminal amino acid of *Der p* II (30); and (b) the homology of this sequence with the equivalent *Der f* II allergen from *Dermatophagoides farinae* (30).

EXAMPLE 6
Isolation and Characterization of cDNA Coding for *Der f* I

MATERIALS AND METHODS
*Dermatophagoides farinae* culture
Mites were purchased from Commonwealth Serum Laboratories, Parkville, Australia.
Construction of the *D. farinae* cDNA λgt11 library
Polyadenylated mRNA was isolated from live *D. farinae* mites and cDNA was synthesized by the RNase H method (Gubler, V. and B. J. Hoffman, *Gene* 25:263–269 (1983)) using a kit (Amersham International, Bucks.). After the addition of EcoRI linkers (New England Biolabs, Beverly, Mass.) the cDNA was ligated to alkaline phosphatase treated λgt11 arms (Promega, Madison, Wis.). The ligated DNA was packaged and plated in *E. coli* Y1090 (r−) to produce a library of 2×10$^4$ recombinants.
Isolation of *Der f* I cDNA clones from the *D. farinae* cDNA λgt11 library
Screening of the library was performed by hybridization with two probes comprising the two *Der p* I cDNA BamHI fragments 1-348 and 349-857 generated by BamHI digestion of a derivative of the *Der p* I cDNA which has had two BamHI restriction sites inserted between amino acid residues −1 and 1 and between residues 116 and 117 by site-directed mutagenesis (Chua, K. Y. et al., *J. Exp. Med.* 167:175–182 (1988)). The probes were radiolabelled with $^{32}$P by nick translation. Phage were plated at 20,000 pfu per 150 mm petri dish and plaques were lifted onto nitrocellulose (Schleicher and Schull, Dassel, FRG), denatured and baked (Maniatis, T. et al., *Molecular Cloning: A Laboratory Manual*, Cold Spring Harbor Laboratory Press (1982)). Prehybridizations were performed for 2 hours at 42° C. in 50% formamide/5×SSCE/1×Denhardt's/poly C (0.1 mg/ml) /poly U(0.1 mg/ml) with hybridization overnight at 42° C. at 10$^6$ cpm/ml. Post hybridization washes consisted of 15 min washes at room temperature with 2×sodium chloride citrate (SSC)/0.1% sodium dodecylsulphate (SDS), 0.5×SSC/0.1% SDS, 0.1×SSC/0.1% SDS successively and a final wash at 50° C. for 30 min in 0.1×SSC/1% SDS.
Isolation of DNA from λgt11 f 1 cDNA clones
Phage DNA from λgt11 f 1 clones was prepared by a rapid isolation procedure. Clarified phage plate lysate (1 ml) was mixed with 270 of 25% wt/vol polyethylene glycol (PEG 6000) in 2.5M NaCl and incubated at room temperature for 15 min. The mixture was then spun for 5 min in a microfuge (Eppendorf, FRG), and the supernatant was removed. The pellet was dissolved in 100 μL of 10 mM Tris/HCl pH8.0 containing 1 mM EDTA and 100 mM NaCl (TE). This DNA preparation was extracted with phenol/TE, the phenol phase was washed with 100 μl TE, the pooled aqueous phases were then extracted another 2 times with phenol/TE, 2 times with Leder phenol (phenol/chloroform/isoamylalcohol; 25:24:1), once with chloroform and the DNA was precipitated by ethanol.

DNA sequencing

To obtain clones for DNA sequence analysis, the λgt11 f1 phage DNA was digested with EcoRI restriction enzyme (Pharmacia, Uppsala, Sweden) and the DNA insert was ligated to EcoRI-digested M13-derived sequencing vectors mp18 and mp19 (Maniatis, T. et al., *Molecular Cloning: A Laboratory Manual,* Cold Spring Harbor Laboratory Press (1982)). Transformation was carried out using *E. coli* TG-1 and sequencing was performed by the dideoxynucleotide chain termination method (Sanger, F. et al., *Proc. Natl. Acad. Sci. USA,* 74:5463–5467 (1977)) using the Sequenase version 2.0 DNA sequencing kit (U.S.B., Cleveland, Ohio).

Polymerase chain reaction (PCR)

PCR was performed by the Taq DNA polymerase method (Saiki, R. K. et al., *Science* 239:487–491 (1988)) using the TaqPaq kit (Biotech International, Bentley, Wash.) and the conditions recommended by the supplier with 10 ng of target DNA and 10 pmol of λgt11 primers (New England BioLabs, Beverly, Mass.).

RESULTS

Isolation of *Der f* I cDNA clones

Two clones expressing the major mite allergen *Der f* I were isolated from the *D. farinae* cDNA λgt11 library by their ability to hybridize with both of the *Der p* I cDNA probes (nucleotides 1-348 and 349-857). This approach was adopted because amino acid sequencing had shown high homology (80%) between these two allergens (Thomas, W. R., et al., *Advances in the Biosciences,* 14:139–147 (1989)). Digestion of the λgt11 f1 clone DNA with EcoRI restriction enzyme to release the cDNA insert produced three *Der f* I cDNA EcoRI fragments: one approximately 800 bases long and a doublet approximately 150 bases long. The *Der f* I cDNA insert was also amplified from the phage DNA by the polymerase chain reaction (PCR) resulting in a PCR product of approximately 1.1-kb. Each *Der f* I cDNA fragment was cloned separately into the M13-derived sequencing vectors mp18 and mp19 and sequenced.

DNA sequence analysis

The nucleotide sequence of *Der f* I cDNA was determined using the sequencing strategy shown in FIG. 9. The complete sequence was shown to be 1084 bases long and included a 335-base long 5' proximal end sequence, a coding region for the entire native *Der f* I protein of 223 amino acids with a derived molecular weight of 25,191 and an 80-base long 3' noncoding region (FIG. 10). The assignment of the threonine residue at position 1 as the NH$_2$-terminal amino acid of *Der f* I was based on data obtained by NH$_2$-terminal amino acid sequencing of the native protein and the predicted amino acid sequence of recombinant *Der p* I (Chua, K. Y. et al., *J. Exp. Med.,* 167:175–182 (1988)). The predicted amino acid sequence of the *Der f* I cDNA in the NH$_2$-terminal region matched completely with that determined at the protein level (FIG. 10).

The complete mature protein coded by a single open reading frame terminating at the TGA stop codon at nucleotide position 42-44 is presumed to be the translation initiation site since the subsequent sequence codes for a typical signal peptide sequence.

Amino Acid Sequence Analysis

The amino acid sequence of *Der f* I predicted by nucleotide analysis is shown in FIG. 10. As shown in the composite alignment of the amino acid sequence of mature *Der p* I and *Der f* I (FIG. 11), high homology was observed between the two proteins. Sequence homology analysis revealed that the *Der f* I protein showed 81% homology with the *Der p* I protein as predicted by previous conventional amino acid sequencing. In particular, the residues making up the active side of *Der p* I, based on those determined for papain, actinidin, cathepsin H, and cathepsin B, are also conserved in the *Der f* I protein. The residues are glutamine (residue 29), glycine, serine and cysteine (residues 33-35), histidine (residue 171) and asparagine, serine and tryptophan (residues 191-193) where the numbering refers to *Der f* I. The predicted mature *Der f* I amino acid sequence contains a potential N-glycosylation site (Asn-Thr-Ser) at position 53-55 which is also present as Asn-Gln-Ser at the equivalent position in *Der p* I.

Analysis of the predicted amino acid sequence of the entire *Der f* I cDNA insert has shown that, as for other cysteine proteases (FIG. 12), the *Der f* I protein has pre- and proform intermediates. As previously mentioned, the methionine residue at position –98 is presumed to be the initiation methionine. This assumption is based on the fact that firstly, the 5' proximal end sequence from residues –98 to –81 is composed predominantly of hydrophobic amino acid residues (72%), which is the characteristic feature of signal peptides (Von Heijne, G., *EMBO J.,* 3:2315–2323 (1984)). Secondly, the lengths of the presumptive pre- (18 amino acid residues) and pro-peptides (80 residues) are similar to those for other cysteine proteases (FIG. 12). Most cysteine proteases examined have about 120 preproenzyme residues (of which an average of 19 residues form the signal peptide) with cathepsin B the smallest with 80 (Ishidoh, K. et al., *FEBS Letters,* 226:32–37 (1987)). *Der f* I falls within this range with a total of 98 preproenzyme residues.

By following the method for predicting signal-sequence cleavage sites outlined in Von Heijne, it is proposed that cleavage from the pre-*Der f* I sequence for proenzyme formation occurs at the signal peptidase cleavage site lying between Ala (–81) and Arg (–80) (Von Heijne, G., *Eur. J. Biochem.,* 133:17–21 (1988) and *J. Mol. Biol.,* 184:99–105 (1985)). Thus, the sequence from residues –98 to –81 codes for the leader peptide while the proenzyme moiety of *Der f* I begins at residue Arg (–80) and ends at residue Glu (–1).

EXAMPLE 7

Isolation and Characterization of cDNA Coding for *Der f* II

MATERIALS AND METHODS

Amino acid sequence analysis Preparation of λgt11 *D. farinae* cDNA ligations

*D. farinae* was purchased from Commonwealth Serum Laboratories, Parkville, Australia, and used to prepare mRNA (polyadenylated RNA) as described (Stewart, G. A. and W. R. Thomas, *Int. Arch. Allergy Appl Immunol.,* 83:384–389 (1987)). The mRNA was suspended at approximately 0.5 μg/μl and 5 μg used to prepare cDNA by the RNase H method (Gubler, U. and Hoffman, B. J., *Gene,* 25:263–269 (1983)) using a kit (Amersham International, Bucks). EcoRI linkers (Amersham, GGAATTCC) were attached according to the method described by Huynh et al., Constructing and screening cDNA libraries in gt10 and gt11, In: Glover, DNA Cloning vol. A practical approach pp. 47–78 IRL Press, Oxford (1985)). The DNA was then digested with EcoRI and recovered from an agarose gel purification by electrophoresis into a DEAE membrane (Schleicher and Schuell, Dassel, FRG, NA-45) according to protocol 6.24 of Sambrook et al., (Sambrook et al., Molecular Cloning: A Laboratory Manual, 2d Ed., Cold Spring Harbor Laboratory Press (1989)), except 0.5M arginine base was used for elution. The cDNA was then ligated in λgt10 and λgt11 at an arms to insert ratio of 2:1. Some was packaged for plaque libraries and an aliquot retained for isolating sequences by polymerase chain reaction as described below.

Isolation of Der f II cDNA by Polymerase Chain Reaction

To isolate Der f II cDNA, an oligonucleotide primer based on the N-terminal sequence of Der p II was made because their amino acid residues are identical in these regions (Heymann, P. W. et al., *J. Allergy Clin. Immunol.*, 83:1055–1087 (1989)). The primer GGATCCGATCAACTCGATGC-3' was used. The first GGATCC encodes a BamH1 site and the following sequence GAT . . . encodes the first four residues of Der p II. For the other primer the λgt11 TTGACACCAGACCAACTGGTAATG-3' reverse primer flanking the EcoRI cloning site was used (New England Biolabs, Beverly, Mass.). The Der p II primer was designed to have approximately 50–60% G–C and to end on the first or second, rather than the third, base of a codon (Gould, S. J. et al., *Proc. Natl. Acad. Sci.*, 86:1934–1938 (1989); Summer, R. and D. Tautz, *Nucleic Acid Res.*, 17:6749 (1989)).

The PCR reactions were carried out in a final reaction volume of 25 μl containing 67 mM Tris-HCL (pH8.8 at 25° C.), 16.6 mM $(NH_4)_2SO_4$, 40 μM dNTPs, 5 mM 2-mercaptoethanol, 6 μM EDTA, 0.2 mg/ml gelatin, 2 mM $MgCl_2$, 10 pmoles of each primer and 2 units of Taq polymerase. Approximately 0.001 μg of target DNA was added and the contents of the tube were mixed and overlayed with paraffin oil. The tubes were initially denatured at 95° C. for 6 minutes, then annealed at 55° C. for 1 minute and extended at 72° C. for 2 minutes. Thereafter for 38 cycles, denaturing was carried out for 30 seconds and annealing and extension as before. In the final (40th) cycle, the extension reaction was increased to 10 minutes to ensure that all amplified products were full length. The annealing temperature was deliberately set slightly lower than the Tm of the oligonucleotide primers (determined by the formula Tm=69.3+0.41 (G+C%)-650/oligo length) to allow for mismatches in the N-terminal primer.

5 μl of the reaction was then checked for amplified bands on a 1% agarose gel. The remainder of the reaction mixture was extracted with chloroform to remove all of the paraffin oil and ethanol precipitated prior to purification of the amplified product on a low melting point agarose gel (Bio-Rad, Richmond, Calif.).

Subcloning of PCR Product

The ends of the purified PCR product were filled in a reaction containing 10 mM Tris HCl, 10 mM $MgCl_2$, 50 mM NaCl, 0.025 mM dNTP and 1 μl of Klenow enzyme in a final volume of 100 μl. The reaction was carried out at 37° C. for 15 minutes and heat inactivated at 70° C. for 10 minutes. The mixture was Leder phenol extracted before ethanol precipitation. The resulting blunt ended DNA was ligated into M13mp118 digested with Sma I in a reaction containing 0.5M ATP, 1×ligase buffer and 1 unit of $T_4$ ligase at 15° C. for 24 hrs and transformed into *E. coli* TG1 made competent by the $CaCl_2$ method. The transformed cells were plated out as a lawn on L+G plates and grown overnight at 37° C.

Preparation of Single-stranded DNA Template for Sequencing

Isolated white plaques were picked using an orange stick into 2.5 ml of an overnight culture of TG1 cells diluted 1 in 100 in 2×TY broth, and grown at 37° C. for 6 hours. The cultures were pelleted and the supernatant removed to a fresh tube. To a 1 ml aliquot of this supernatant 270 μl of 20% polyethylene glycol, 2.5M NaCl was added and the tube was vortexed before allowing it to stand at room temperature (RT) for 15 minutes. This was then spun down again and all traces of the supernatant were removed from the tube. The pellet was then resuspended in 100 μl of 1×TE buffer. At least 2 phenol:TE extractions were done, followed by 1 Leder phenol extraction and a $CHCl_3$ extraction. The DNA was precipitated in ethanol and resuspended in a final volume of 20 μl of TE buffer.

DNA Analysis

DNA sequencing was performed with the dideoxynucleotide chain termination (Sanger, F. et al., *Proc. Natl. Acad. Sci.*, 74:5463–5467 (1977)) using DNA produced from M13 derived vectors mp18 and mp19 in *E. coli* TG1 and T4 DNA polymerase (Sequenase version 2.0, USB Corp., Cleveland, Ohio; Restriction endonucleases were from Toyobo, (Osaka, Japan). All general procedures were by standard techniques (Sambrook, J. et al., A Laboratory Manual, 2d Ed. Cold Spring Harbor Laboratory Press (1989)). The sequence analysis was performed using the Mac Vector Software (IBI, New Haven, Conn.).

RESULTS

*D. farinae* cDNA ligated in λgt11 was used to amplify a sequence using an oligonucleotide primer with homology to nucleotides coding for the 4 N-terminal residues of Der p II and a reverse primer for the λgt11 sequence flanking the coding site. Two major bands of about 500 bp and 300 bp were obtained when the product was gel electrophoresed. These were ligated into M13 mp18 and a number of clones containing the 500 bp fragment were analyzed by DNA sequencing. Three clones produced sequence data from the N-terminal primer end and one from the other orientation. Where the sequence data from the two directions overlapped, a complete match was found. One of the clones read from the N-terminal primer, contained a one-base deletion which shifted the reading frame. It was deduced to be a copying error, as the translated sequence from the other two clones matched the protein sequence for the first 20 amino acid residues of the allergen.

The sequence of the clones showing consensus and producing a correct reading frame is shown in FIG. 14, along with the inferred amino acid sequence. It coded for a 129 residue protein with no N-glycosylation site and a calculated molecular weight of 14,021 kD. No homology was found when compared to other proteins on the GenBank data base (61.0 release). It did, however, show 88% amino acid residue homology with Der p II shown in the alignment in FIG. 16. Seven out of the 16 changes were conservative. The conserved residues also include all the cysteines present at positions 8, 21, 27, 73 and 119. There was also considerable nucleotide homology, although the restriction enzyme map generated from the sequence data for commonly used enzymes is different from Der p II (FIG. 15). The hydrophobicity plots of the translated sequence of Der f II and Der p II shown in FIG. 17 are almost identical.

EXAMPLE 8

Determination of Nucleotide Sequence Polymorphisms in the Der p II, Der p II and Der f II Allergens It was expected that there were sequence polymorphisms in the nucleic acid sequence coding for Der p I, Der p II, Der f I and Der f II, due to natural allelic variation among individual mites. Several nucleotide and resulting amino acid sequence polymorphisms were discovered during the sequencing of different Der p I, Der p II and Der f II clones. The amino acid sequence polymorphisms are shown in FIGS. 18, 19 and 20.

The original Der p I λgt11 cDNA library was reprobed with cDNA obtained from the λgt11 p1(13T) clone to identify new clones. Similarly, the λgt11 cDNA library of Der p II was reprobed with cDNA obtained from the λgt11 pII(C1) clone to identify additional Der p II clones. These clones were isolated, sequenced and found to contain nucleotide and resulting amino acid sequence polymorphisms (see FIGS. 18 and 19).

Four Der p I clones, (b), (c), (d) and (e) were sequenced, as shown in FIG. 18. Clone Der p I(d) was found to contain the following polymorphisms relative to the clone Der p I(a) sequence: (1) the codon for amino acid residue 136 was ACC rather than AGC, which results in a predicted amino acid substitution of Thr for Ser; (2) the codon for amino acid residue 149 had a silent mutation, GCT rather than GCA; and (3) the codon for amino acid residue 215 was CAA rather than GAA; which results in a predicted amino acid substitution of Gln for Glu.

The Der p II clones, Der p II(1) and Der p II(2) were sequenced as shown in FIG. 19. Clone Der p II(2) was found to have the codon TCA, rather than ACA at amino acid residue 47, which results in a predicted amino acid substitution of Ser for Thr. This clone also was found to have the codon AAT at amino acid residue 113 rather than GAT, which results in a predicted amino acid substitution of Asn for Asp. The codon for amino acid 127 of this clone was found to be CTC rather than ATC. This change in codon 127 results in a predicted amino acid substitution of Leu for Ile.

Additional Der f II cDNA clones containing nucleic acid and resulting amino acid sequence polymorphisms were obtained from PCR reactions using cDNA prepared with RNA isolated from D. farinae mites (Commonwealth Serum Laboratories, Parksville, Australia). cDNA was prepared and ligated in λgt10 as previously described (Trudinger e al. (1991) Clin. Exp. Allergy 21:33–37). The clones described below were isolated following PCR of the λgt10 library using a 5' primer, which had the sequence 5'-GGATCCGATCAAGTCGATGT-3'. The nucleotides 5'-GGATCC-3' of the 5' primer correspond to a Bam HI endonuclease site added for cloning purposes. The remaining nucleotides of the 5' primer, 5'-GATCAAGTCGATGT-3' correspond to the first 4 amino acids of Der p II (Chua et al. (1990) Int. Arch. Allergy Clin. Immunol. 91:118–123) as described in Trudinger et al. ((1991) Clin. Exp. Allergy 21:33–37). The 3' primer, which has the sequence 5'-TTGACACCAGACCAACTGGTAATG-3', corresponds to a sequence of the λgt10 cloning vector (Trudinger et al. supra).

PCR was performed as described (Trudinger et al. supra) and four Der f II clones, MT3, MT5, MT16 and MT18, were sequenced, as shown in FIG. 20. Three clones were sequenced that had potential polymorphisms relative to the published Der f II sequence (Trudinger at a. supra). The codon for amino acid 52 of clone MT19 was ATT rather than the published ACT (Trudinger et a. supra). This change in codon 52 of clone MT18 would result in a predicted amino acid change from Thr to Ile. Clone MT5 contained three changes from the published sequence (Trudinger e a supra): (1) the codon for amino acid 11 was AGC rather than the published AAC (Trudinger al.), which results in a predicted amino acid substitution of Ser for Asn; (2) the codon for amino acid 52 was ATT, rather than the published ACT (Trudinger et al. supra), which results in a predicted amino acid substitution of Ile for Thr; and (3) the codon for amino acid 88 was ATC rather than the published GCC (Trudinger et al. supra), which results in a predicted amino acid substitution of Ile for Ala. Clone MT16 had a silent mutation in the codon for amino acid 68 (ATC versus the published ATT (Trudinger et al. supra) that did not change the predicted amino acid at this residue. The following substitutes were also observed by Yuuki et al. (Jpn.J.Allergol. 6:557–561, 1990); Ile at residue 52, Ile at residue 54 and Ile at residue 88.

Equivalents

Those skilled in the art will recognize, or be able to ascertain using no more than routine experimentation, many equivalents to the specific embodiments of the invention described herein. Such equivalents are intended to be encompassed by the following claims.

REFERENCES

1. Ford, A. W., Rawle, F. C., Lind, P., Spieksma, F. T. M., Lowenstein, H., Platts-Mills, T. A. E. (1985). Standardization of Dermatophagoides pteronyssinus. Assessment of potency and allergen content in the coded extracts. Int. Arch. Allergy Appl. Immunol. 76:58–67.
2. Lind, P., Lowenstein, H. (1983). Identification of allergens in Dermatophagoides pteronyssinus mite body extract by crossed radioimmunelectrophoresis with two different rabbit antibody pools. Scand. J. Immunol. 17:263–273.
3. Krilis, S., Baldo, B. A., Basten, A. (1984). Antigens and allergens from the common house dust mite Dermatophagoides pteronyssinus Part II. Identification of the major IgE binding antigens by crossed radioimmunelectrophoresis. J. Allergy. Clin. Immunol. 74:142–146.
4. Tovey, E. R., Chapman, M. D., Platts-Mills, T. A. E. (1981). Mite faeces are a major source of house dust allergens. Nature 289:592–593.
5. Gubler, U., Hoffman, B. J. (1983). A simple and very efficient method for generating cDNA libraries. Gene 25:263–269.
6. Huynh, T. V., Young, R. A., Davis, R. W. Constructing and screening cDNA libraries in λ10 and λgt11. p48–78 in DNA Cloning Col. 1, A practical approach. Ed. D. M. Glover, IRL press.
7. Stewart, G. A., Thomas, W. R. (1987). In vitro translation of messenger RNA from the house mite Dermatophagoides pteronyssinus. Int. Arch. Allergy Appl. Immunol. 83:384–389.
8. Thomas, W. R., Rossi, A. A. (1986). Molecular cloning of DNA coding for outer membrane proteins of Haemophilus influenzae type b. Infection and Immunity 52:812–817.
9. Simpson, R. J., Smith, J. A., Mortiz, R. L., O'Hare, M. J., Rudland, P. S., Morrison, J. R., Lloyd, C. J., Grego, B., Burgess, A. W. and Nice, E. L. (1985). Rat Epidermal Growth Factor: Complete amino acid sequence. Eur. J. Biochem. 153:629–637.
10. Maniatis, T., Fritsch, E. F., Sambrook, J. (1982). Molecular cloning. A Laboratory Manual, Cold Spring Harbor Laboratory.
11. Sanger, F., Nicklen, S., Coulson, A. R. (1977). DNA sequencing with chain-terminating inhibitors. Proc. Natl. Acad. Sci. 74:5463–5467.
12. Heyman, P. W., Chapman, M. D., Platts-Mills, T. A. E. (1986). Antigen Der f I from the house dust mite Dermatophagoides farinae: Structural comparison with Der p I from Dermatophagoides pteronyssinus and epitope specificity of murine IgG and human IgE antibodies. J. Immunol, 137:2841–2847.
13. Voorhorst, R., Spieksma-Boezeman, M. I. A., and Spieksma, F. Th. M. (1964). Is a mite (Dermatophagoides sp) the producer of the house dust allergen. Allerg. Asthma. 10:329.
14. Voorhorst, R., Spieksma, F. Th. M., Varekamp, H., Leupen, M. J. and Lyklema, A. W., (1967). The house dust mite (*Dermatophagoides pteronyssinus*) and the allergens it produces. Identity with the house dust allergen. *J Allergy*. 3:325.
15. Stewart, G. A. and Thomas, W. R. (1987). In vitro translation of messenger RNA from the house dust mite *Dermatophagoides pteronyssinus*. *Int. Arch. Allergy Appl. Immunol.* 83:384.
16. Messing, J. (1983). New M13 vectors for cloning. *Methods Enzymol.* 101:20.
17. Stewart, G. A., Simpson, R. J., Thomas, W. R. and Turner, K. J. (1986). The physiochemical characterization of a major protein allergen from the house dust mite, EP. *Asian Pac. J. Allergy Immunol.* 5:71.
18. Kozak, M. (1984). Compilation and analysis of sequences upstream from the translational start site in eukaryotic mRNAs. *Nucleic. Acids Res.* 12:857.
19. San Segundo, B., Chain, S. J. and Steiner, D. F. (1985). Identification of cDNA clones encoding a precursor of rat liver cathepsin B. *Proc. Natl. Acad. Sci. USA.* 82:2320.
20. Portnoy, D. A., Erickson, A. H., Kochan, J., Ravetch, J. V. and Unkeless, J. C. (1986). Cloning and characterization of a mouse cysteine proteinase. *J. Biol. Chem.* 261:14697.
21. Williams, J. G., North, M. J. and Mahbubani, H. (1985). A developmentally regulated cysteine proteinase in *Dictyostelium discoideum*. *EMBO (Eur. Mol. Biol. Organ.) J.* 4:999.
22. Hopp, T. P. (1986). Protein surface analysis. Method for identifying antigenic determinants and other interaction sites. *J. Immunol, Methods.* 88:1.
23. Von Heijne, G. (1984). Analysis of the distribution of charged residues in the N-terminal region of signal sequences: implications of protein export in prokaryotic and eukaryotic cells. *EMBO (Eur. Mol. Biol. Organ.) J.* 3:2315.
24. Ullrich, A., Shine, J., Chirgwin, J., Pictet, R., Tischer, E., Rutter, W. J. and Goodman, H. W. (1977). Rat insulin genes: Construction of plasmids containing th coding sequences. *Science* (Wash. DC) 196:1313.
25. Carne, T. and Scheele, G. (1985). Cell Biology of the Secretory Process. M. Cantin, editor. S. Karger AG, Basel. 73.
26. Smith, D. and Johnson (1988), *Gene* (in press).
27. Thomas, W. R. and Rossi, A. A. (1986). Molecular cloning of DNA coding for outer membrane proteins of *Haemophilus influenzae* Type b. *Infection and Immunity* 52:812–817.
28. Thomas, W. R., Stewart, G. A., Simpson, R. J., Chua, K. Y., Plozza, T. M., Dilworth, Dr. U., Nisbet, A. and Turner, K. J. (1987). Cloning and expression of DNA coding for the major house dust mite allergen *Der p* I in *Escherichia coli*. *Int. Arch. Allergy Appl. Immunol.* 85:127–129.
29. Stewart, G. A. and Holt, P. G. (1987). Immunogenicity and tolerogenicity of a major house dust mite allergen *Der p* I. *Int. Arch. Allergy Appl. Immunol.* 83:44–51.
31. Chapman, M. D., Heymann, P. W. and Platts-Mills, T. A. E. (1987). Mite allergens 1. Epitope mapping of major dust mite (Dermatophagoides) allergens using monoclonal antibodies. Mite Allergy—A World Wide Problem. Ed. A. L. deWeck and A. Todt. The UCB Institute of Allergy.

We claim:

1. An isolated peptide comprising a portion of a *Der f* II protein allergen having the following amino acid sequence (SEQ ID NO:13), wherein the peptide comprises at least one T cell epitope and at least one amino acid sequence polymorphism selected from the group consisting of $Xaa_1$, $Xaa_2$, $Xaa_3$, $Xaa_4$, $Xaa_5$ and $Xaa_6$:

Asp Gln Val Asp Val Lys Asp Cys Ala Asn $Xaa_1$ Glu Ile Lys Lys Val Met Val Asp Gly Cys His Gly Ser Asp Pro Cys Ile Ile His Arg Gly Lys Pro Phe Thr Leu Glu Ala Leu Phe Asp Ala Asn Gln Asn Thr Lys Thr Ala Lys $Xaa_2$ Glu $Xaa_3$ Lys Ala Ser Leu Asp Gly Leu Glu Ile Asp Val Pro Gly Ile Asp Thr Asn Ala Cys His Phe $Xaa_4$ Lys Cys Pro Leu Val Lys Gly Gln Gln Tyr Asp $Xaa_5$ Lys Tyr Thr Trp Asn Val Pro Lys Ile Ala Pro Lys Ser Glu Asn Val Val Val Thr Val Lys Leu $Xaa_6$ Gly Asp Asn Gly Val Leu Ala Cys Ala Ile Ala Thr His Ala Lys Ile Arg Asp (SEQ ID NO: 13)

where $Xaa_1$ is selected from the group consisting of Asn and Ser;

where $Xaa_2$ is selected from the group consisting of Thr and Ile;

where $Xaa_3$ is selected from the group consisting of Ile and Thr;

where $Xaa_4$ is selected from the group consisting of Met and Val;

where $Xaa_5$ is selected from the group consisting of Ala and Ile; and where $Xaa_6$ is selected from the group consisting of Val and Ile, with the proviso that, when $Xaa_1$ is Asn, then $Xaa_3$ is Thr; and
when $Xaa_3$ is Ile, then $Xaa_1$ is Ser.

2. A therapeutic composition comprising the protein allergen or peptide of claim 1 and a pharmaceutically acceptable carrier or diluent.

3. The peptide of claim 1 wherein $Xaa_1$ is Asn, $Xaa_2$ is Ile, $Xaa_3$ is Thr, $Xaa_4$ is Met, $Xaa_5$ is Ala, and $Xaa_6$ is Val.

4. A therapeutic composition comprising a peptide of claim 1 or claim 3, or a combination of said peptides, and a pharmaceutically acceptable carrier or diluent.

5. A diagnostic reagent comprising a peptide of claim 1 or claim 3, or a combination of said peptides.

* * * * *